US011475985B2

(12) United States Patent
Colburn et al.

(10) Patent No.: US 11,475,985 B2
(45) Date of Patent: Oct. 18, 2022

(54) GENERATION OF REAL-TIME TRIGGER-BASED DIGITAL FEED

(71) Applicant: Alegeus Technologies, LLC, Waltham, MA (US)

(72) Inventors: Brian Colburn, Sudbury, MA (US); Christopher Rodkey, Beverly, MA (US)

(73) Assignee: Alegeus Technologies, LLC, Waltham, MA (US)

( * ) Notice: Subject to any disclaimer, the term of this patent is extended or adjusted under 35 U.S.C. 154(b) by 41 days.

(21) Appl. No.: 17/214,153

(22) Filed: Mar. 26, 2021

(65) Prior Publication Data

US 2022/0028505 A1 Jan. 27, 2022

Related U.S. Application Data

(60) Provisional application No. 63/056,294, filed on Jul. 24, 2020.

(51) Int. Cl.
*G16H 10/60* (2018.01)
*G06N 20/00* (2019.01)

(52) U.S. Cl.
CPC .......... *G16H 10/60* (2018.01); *G06N 20/00* (2019.01)

(58) Field of Classification Search
CPC ......... G16H 10/60; G06F 19/30; G06F 19/32; G06F 19/34; G06Q 50/22; G06N 20/00; G06N 20/10; G06N 20/20
See application file for complete search history.

(56) References Cited

U.S. PATENT DOCUMENTS

2005/0234742 A1\* 10/2005 Hodgdon
2012/0166267 A1\* 6/2012 Beatty ............... G06Q 30/0219
705/14.21

(Continued)

*Primary Examiner* — Michael Tomaszewski
*Assistant Examiner* — William T. Monticello
(74) *Attorney, Agent, or Firm* — Foley & Lardner LLP

(57) ABSTRACT

At least one aspect of this technical solution is directed to a system for invoking account opportunities for support accounts, the system including a data processing system comprising memory and one or more processors to receive, from one or more external data sources, a plurality of opportunity events indicating modifications for candidate electronic transactions, select, in response to receipt of the plurality of opportunity events, a participant object including a support service identifier associated with a support service, and a participant service identifier associated with a participant service, filter the plurality of opportunity events based at least on a first opportunity metric associated with the participant object to construct a plurality of opportunity objects, rank the plurality of opportunity objects based at least on a determination that the opportunity object satisfies a second opportunity metric associated with the participant object, transmit, to a computing device linked with the participant object, the ranked plurality of opportunity objects, receive, from the computing device, a selection of one or more of the ranked plurality of opportunity objects, generate, responsive to the selection of the one or more of the ranked opportunity objects, a link between the participant object and the support service, and authorize the participant object to the support service based on the link.

20 Claims, 11 Drawing Sheets

(56) References Cited

U.S. PATENT DOCUMENTS

| | | |
|---|---|---|
| 2013/0060623 A1* | 3/2013 | Walker |
| 2014/0200909 A1* | 7/2014 | Felix |
| 2014/0257834 A1* | 9/2014 | Johnson |
| 2017/0148034 A1* | 5/2017 | Sharma .............. G06Q 30/0201 |
| 2018/0158090 A1* | 6/2018 | Glynn et al. |
| 2020/0104935 A1* | 4/2020 | Schmitt |
| 2020/0143273 A1* | 4/2020 | Bettencourt-Silva |
| 2021/0103935 A1* | 4/2021 | Liao .................... G06Q 30/016 |

* cited by examiner

GENERATION OF REAL-TIME TRIGGER-BASED DIGITAL FEED

CROSS-REFERENCE TO RELATED PATENT APPLICATIONS

This application claims the benefit of priority under 35 U.S.C. § 119 to U.S. Provisional Patent Application Ser. No. 63/056,294, entitled "GENERATION OF REAL-TIME TRIGGER-BASED DIGITAL FEED," filed Jul. 24, 2020, which is hereby incorporated by reference herein in its entirety.

TECHNICAL FIELD

This disclosure relates generally to digital healthcare infrastructure, and more particularly to generation of a real-time trigger-based digital feed.

BACKGROUND

Participants of a health care program can conduct an electronic transaction for goods or services. Due to the large number of available sources for goods or services, and the varying parameters associated with electronic transactions, it can be challenging to efficiently and accurately select a source for the goods or services for a participant without wasting resource utilization or introducing latency or delays.

SUMMARY OF THE DISCLOSURE

Health care opportunities are increasing in complexity and scope in response to the expansion of health care services available to health care consumers. Participants in various health care support programs and health care accounts face increasingly complex and interwoven opportunities with time-sensitive conditions and complex interdependencies. However, conventional systems may not effectively feed opportunities associated with such services and accounts effectively or timely to a participant, resulting in a loss of opportunities due to lack of computational technological systems to rapidly and securely communicate with heterogeneous systems centered on a participant's associations with services coupled to those systems. Thus, systems and methods of this technical solution provide can generate a real-time trigger-based digital feed.

At least one aspect of this technical solution is directed to a system for invoking account opportunities for support accounts, the system including a data processing system comprising memory and one or more processors to receive, from one or more external data sources, a plurality of opportunity events indicating modifications for candidate electronic transactions, select, in response to receipt of the plurality of opportunity events, a participant object including a support service identifier associated with a support service, and a participant service identifier associated with a participant service, filter the plurality of opportunity events based at least on a first opportunity metric associated with the participant object to construct a plurality of opportunity objects, rank the plurality of opportunity objects based at least on a determination that the opportunity object satisfies a second opportunity metric associated with the participant object, transmit, to a computing device linked with the participant object, the ranked plurality of opportunity objects, receive, from the computing device, a selection of one or more of the ranked plurality of opportunity objects, generate, responsive to the selection of the one or more of the ranked opportunity objects, a link between the participant object and the support service, and authorize the participant object to the support service based on the link.

At least one aspect of this technical solution is directed to a system where the data processing system further includes a machine learning engine communicatively coupled to the memory and the one or more processors, and is operable to configure, by the processor, a machine learning engine based at least partially on the received selection of the one or more ranked opportunity objects by modifying at least one of the first opportunity metric and the second opportunity metric.

At least one aspect of this technical solution is directed to system where the data processing system is further operable to filter, by the processor, the opportunity objects based at least partially on a determination that one or more of the opportunity objects satisfy a timestamp threshold associated with the participant object.

At least one aspect of this technical solution is directed to a system where the received selection is received at a selection time satisfying the timestamp threshold.

At least one aspect of this technical solution is directed to a system where the machine learning engine is further operable to modify at least one of the first opportunity metric and the second opportunity metric.

At least one aspect of this technical solution is directed to a system where the first opportunity metric comprises a participant compatibility metric associated with the participant service and the support service.

At least one aspect of this technical solution is directed to a system of claim 1, where the second opportunity metric comprises a participant interaction metric associated with the participant object and at least one of the opportunity objects.

At least one aspect of this technical solution is directed to a system where the opportunity event comprises a state change of the participant object.

At least one aspect of this technical solution is directed to a system where the opportunity event comprises a state change of the participant service.

At least one aspect of this technical solution is directed to a system where the support service identifier identifies a support record of an individual associated with the support service and the participant service.

At least one aspect of this technical solution is directed to a system where the data processing system is further operable to obtain, by the processor, the support service at a remote support account system.

At least one aspect of this technical solution is directed to a system where the data processing system is further operable to obtain, by the processor, the participant service at a remote financial account system.

At least one aspect of this technical solution is directed to a system where the data processing system is further operable to obtain the participant object and the participant service identifier by a first remote communication interface.

At least one aspect of this technical solution is directed to a system where the data processing system is further operable to obtain the opportunity objects by a second remote communication interface.

At least one aspect of this technical solution is directed to a method for invoking account opportunities for particular support care accounts, the method including receiving, from one or more external data sources, a plurality of opportunity events indicating modifications of candidate electronic transactions, selecting, in response to receipt of the plurality of opportunity events, a participant object including a support service identifier associated with a support service, and a participant service identifier associated with a participant service, filtering the plurality of opportunity events based at least on a first opportunity metric associated with the participant object to construct a plurality of opportunity objects, ranking the plurality of opportunity objects based at least on a determination that the opportunity object satisfies a second opportunity metric associated with the participant object, transmitting, to a computing device linked with the participant object, the ranked plurality of opportunity objects, receiving, from the computing device, a selection of one or more of the ranked plurality of opportunity objects, and generating, in response to the selection of the one or more of the ranked opportunity objects, a link between the participant object and the support service, and authorizing the participant object to the support service based on the link.

At least one aspect of this technical solution is directed to a method further including configuring a machine learning engine based at least partially on the received selection of the one or more ranked opportunity objects, and modifying at least one of the first opportunity metric and the second opportunity metric in response to the configuring the machine learning engine.

At least one aspect of this technical solution is directed to a method where the filtering further includes filtering the opportunity objects based at least partially on a determination that one or more of the opportunity objects satisfy a timestamp threshold associated with the participant object.

At least one aspect of this technical solution is directed to a method where the received selection is received at a selection time satisfying the timestamp threshold.

At least one aspect of this technical solution is directed to a computer readable medium including one or more instructions stored thereon and executable by a processor to receive, from one or more external data sources, a plurality of opportunity events indicating modifications for candidate electronic transactions, select, at the processor, in response to receipt of the plurality of opportunity events, a participant object including a support service identifier associated with a support service, and a participant service identifier associated with a participant service, and filter, by the processor, the plurality of opportunity events based at least on a first opportunity metric associated with the participant object, and rank, by the processor, the plurality of opportunity objects based at least on a determination that the opportunity object satisfies a second opportunity metric associated with the participant object, transmit, to a computing device linked with the participant object, the ranked plurality of opportunity objects, receive, by the processor, from the computing device, a selection of one or more of the ranked plurality of opportunity objects, generate, responsive to the selection of the one or more of the ranked opportunity objects, a link between the participant object and the support service, and authorize the participant object to the support service based on the link.

At least one aspect of this technical solution is directed to a computer readable medium further including one or more instructions executable by a processor to configure a machine learning engine based at least partially on the received selection of the one or more ranked opportunity objects by modifying at least one of the first opportunity metric and the second opportunity metric.

BRIEF DESCRIPTION OF THE DRAWINGS

These and other aspects and features of the present implementations will become apparent to those ordinarily skilled in the art upon review of the following description of specific implementations in conjunction with the accompanying figures, wherein.

DETAILED DESCRIPTION

Figure 1A:
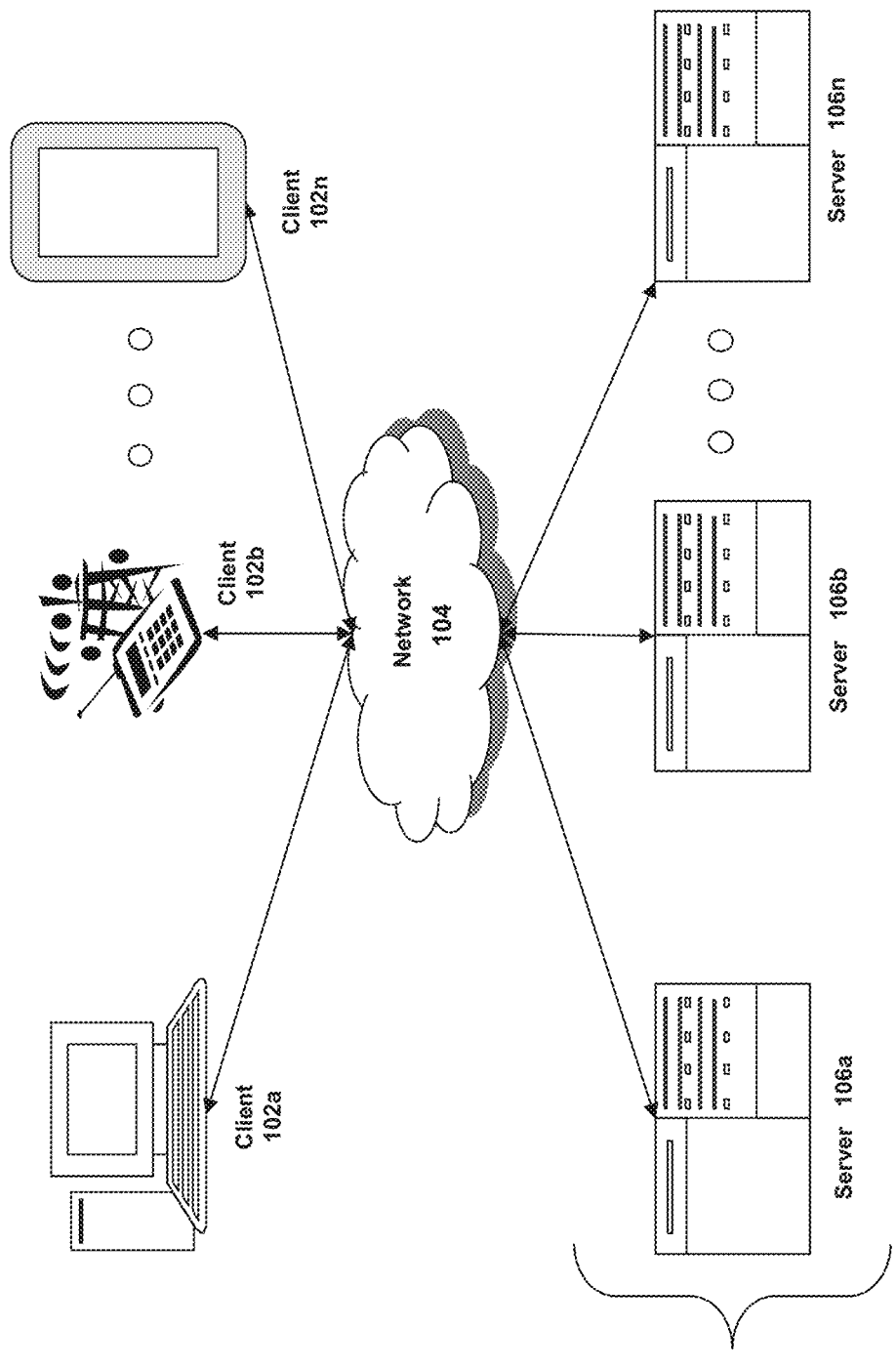
FIG. 1A illustrates an example network environment including a client device in communication with a server device, in accordance with present implementations.

The present implementations will now be described in detail with reference to the drawings, which are provided as illustrative examples of the implementations so as to enable those skilled in the art to practice the implementations and alternatives apparent to those skilled in the art. Notably, the figures and examples below are not meant to limit the scope of the present implementations to a single implementation, but other implementations are possible by way of interchange of some or all of the described or illustrated elements. Moreover, where certain elements of the present implementations can be partially or fully implemented using known components, only those portions of such known components that are necessary for an understanding of the present implementations will be described, and detailed descriptions of other portions of such known components will be omitted so as not to obscure the present implementations. Implementations described as being implemented in software should not be limited thereto, but can include implementations implemented in hardware, or combinations of software and hardware, and vice-versa, as will be apparent to those skilled in the art, unless otherwise specified herein. In the present specification, an implementation showing a singular component should not be considered limiting; rather, the present disclosure is intended to encompass other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present implementations encompass present and future known equivalents to the known components referred to herein by way of illustration.

A data processing system can assist in identifying and executing health care opportunities relevant to health conditions and support services related to and individualized to particular participants of the data processing system and one or more support services. The data processing system can determine conditions, triggers or similar states or changes in state of support services or offerings to search for opportunities relevant to individual participants. Actions executable by the data processing system can include identifying new opportunities based on information from one or more third party data sources, creating a list of opportunities enumerated or ranked based on relevance to the participant, and proactively providing various relevant opportunities to a participant by a graphical user interface at a participant computing device.

The data processing system can also invoke, receive, or apply, for example, various triggers to determine when to identify new opportunities. These triggers can include onboarding of a new participant to the data processing system, a card swipe by the participant at a merchant payment portal, point-of-sale terminal, for example, a real-time transaction between the participant and a linked health service account or service. The data processing system can also associate triggers with, for example, a particular calendar event, a particular season or seasonality recurrence, or based on any other time-interval proactively established by the data processing system, the participant, or the third party external support service, for example. The data processing system can receive, generate, process, modify, or transform, for example, data from external third party systems including prescriptions, drug composition and tracking information, preferred or "home" pharmacy selections, insurance plan memberships and selections, chronic conditions, insurance claim history. Data can also include insurance and spending history including health savings accounts, and credit card transactions, for example. The data processing system can support multiple types of outputs, including filters, notifications regarding various aspects, fields or operations of opportunities, changing configurations or operations of external accounts including 401(k), health savings accounts, and flexible spending accounts, for example.

The data processing system can also include or interface with a machine learning system to predict optimal opportunities for individual users. A machine learning system of the data processing system can validate feedback responses based on subsequent transaction data, and can determine whether or not to send notifications based on interaction feedback indicating a likelihood of a participant to select, execute, or view, for example, a particular opportunity.

Opportunities can be opportunity events and opportunity objects. Opportunity events can represent changes in state, for example, of a service or product relevant to a participant. Opportunity objects can encapsulate various characteristics of opportunities relevant to a participant, and can facilitate execution of various transaction with external healthcare support services, platforms, or accounts, for example. Opportunities can be related to pharmacy services, and can prompt a user to save expense in transacting with a particular pharmacy for prescriptions or other goods or service with that pharmacy. Savings could take the form of coupons directly with the pharmacy, or partnerships with external discount programs, for example. Opportunities can also be related to financial or monetary accounts assigned to the participant. For example, an opportunity can allow a participant to maximize or modify a recurring or one-time contribution to a financial account. Accounts can include health-savings accounts, flexible spending accounts, checking accounts, credit accounts, and rewards accounts, for example. One-time or recurring contributions can also include annual or year-end contributions. For example, if a participant still has money left in their FSA within 90 days of the end of their plan year, the data processing system can recognize that state as an opportunity event, and generate and provide an opportunity object including a targeted coupon, dependent on their balance, to shop at a store accepting flexible spending account funds.

For purposes of reading the description of the various implementations below, the following descriptions of the sections of the specification and their respective contents can be helpful:

Section A describes a network environment and computing environment which can be useful for practicing implementations described herein.

Section B describes implementations of systems and methods for generation of a real-time trigger-based digital feed.

A. Computing and Network Environment

Prior to discussing specific implementations of the present solution, it can be helpful to describe aspects of the operating environment as well as associated system components (e.g., hardware elements) in connection with the methods and systems described herein. Referring to FIG. 1A, an implementation of a network environment is depicted. In brief overview, the network environment includes one or more clients 102a-102n (also generally referred to as local machine(s) 102, client(s) 102, client node(s) 102, client machine(s) 102, client computer(s) 102, client device(s) 102, endpoint(s) 102, or endpoint node(s) 102) in communication with one or more servers 106a-106n (also generally referred to as server(s) 106, node 106, or remote machine(s) 106) via one or more networks 104. In some implementations, a client 102 has the capacity to function as both a client node seeking obtain to resources provided by a server and as a server providing obtain to hosted resources for other clients 102a-102n.

Although FIG. 1A shows a network 104 between the clients 102 and the servers 106, the clients 102 and the servers 106 can be on the same network 104. In some implementations, there are multiple networks 104 between the clients 102 and the servers 106. In one of these implementations, a network 104' (not shown) can be a private network and a network 104 can be a public network. In another of these implementations, a network 104 can be a private network and a network 104' a public network. In still another of these implementations, networks 104 and 104' can both be private networks.

The network 104 can be connected via wired or wireless links. Wired links can include Digital Subscriber Line (DSL), coaxial cable lines, or optical fiber lines. The wireless links can include BLUETOOTH, Wi-Fi, Worldwide Interoperability for Microwave Access (WiMAX), an infrared channel or satellite band. The wireless links can also include any cellular network standards used to communicate among mobile devices, including standards that qualify as 1G, 2G, 3G, or 4G. The network standards can qualify as one or more generation of mobile telecommunication standards by fulfilling a specification or standards such as the specifications maintained by International Telecommunication Union. The 3G standards, for example, can correspond to the International Mobile Telecommunications-2000 (IMT-2000) specification, and the 4G standards can correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards can use various channel access methods e.g. FDMA, TDMA, CDMA, or SDMA. In some implementations, different types of data can be transmitted via different links and standards. In other implementations, the same types of data can be transmitted via different links and standards.

The network 104 can be any type and/or form of network. The geographical scope of the network 104 can vary widely and the network 104 can be a body area network (BAN), a personal area network (PAN), a local-area network (LAN), e.g. Intranet, a metropolitan area network (MAN), a wide area network (WAN), or the Internet. The topology of the network 104 can be of any form and can include, e.g., any of the following: point-to-point, bus, star, ring, mesh, or tree. The network 104 can be an overlay network which is virtual and sits on top of one or more layers of other networks 104'. The network 104 can be of any such network topology as known to those ordinarily skilled in the art capable of supporting the operations described herein. The network 104 can utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite can include application layer, transport layer, internet layer (including, e.g., IPv6), or the link layer. The network 104 can be a type of a broadcast network, a telecommunications network, a data communication network, or a computer network.

In some implementations, the system can include multiple, logically-grouped servers 106. In one of these implementations, the logical group of servers can be referred to as a server farm 38 or a machine farm 38. In another of these implementations, the servers 106 can be geographically dispersed. In other implementations, a machine farm 38 can be administered as a single entity. In still other implementations, the machine farm 38 includes a plurality of machine farms 38. The servers 106 within each machine farm 38 can be heterogeneous—one or more of the servers 106 or machines 106 can operate according to one type of operating system platform (e.g., WINDOWS NT, manufactured by Microsoft Corp. of Redmond, Wash.), while one or more of the other servers 106 can operate on according to another type of operating system platform (e.g., Unix, Linux, or Mac OS X).

In one implementation, servers 106 in the machine farm 38 can be stored in high-density rack systems, along with associated storage systems, and located in an enterprise data center. In this implementation, consolidating the servers 106 in this way can improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 can be interconnected using a wide-area network (WAN) connection or a metropolitan-area network (MAN) connection. For example, a machine farm 38 can include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 can include one or more servers 106 operating according to a type of operating system, while one or more other servers 106 execute one or more types of hypervisors rather than operating systems. In these implementations, hypervisors can be used to emulate virtual hardware, partition physical hardware, virtualize physical hardware, and execute virtual machines that provide access to computing environments, allowing multiple operating systems to run concurrently on a host computer. Native hypervisors can run directly on the host computer. Hypervisors can include VMware ESX/ESXi, manufactured by VMWare, Inc., of Palo Alto, Calif.; the Xen hypervisor, an open source product whose development is overseen by Citrix Systems, Inc.; the HYPER-V hypervisors provided by Microsoft or others. Hosted hypervisors can run within an operating system on a second software level. Examples of hosted hypervisors can include VMware Workstation and VIRTUALBOX.

Management of the machine farm 38 can be de-centralized. For example, one or more servers 106 can comprise components, subsystems and modules to support one or more management services for the machine farm 38. In one of these implementations, one or more servers 106 provide functionality for management of dynamic data, including techniques for handling failover, data replication, and increasing the robustness of the machine farm 38. Each server 106 can communicate with a persistent store and, in some implementations, with a dynamic store.

Server 106 can be a file server, application server, web server, proxy server, appliance, network appliance, gateway, gateway server, virtualization server, deployment server, SSL VPN server, or firewall. In one implementation, the server 106 can be referred to as a remote machine or a node. In another implementation, a plurality of nodes 290 can be in the path between any two communicating servers.

Figure 1B:
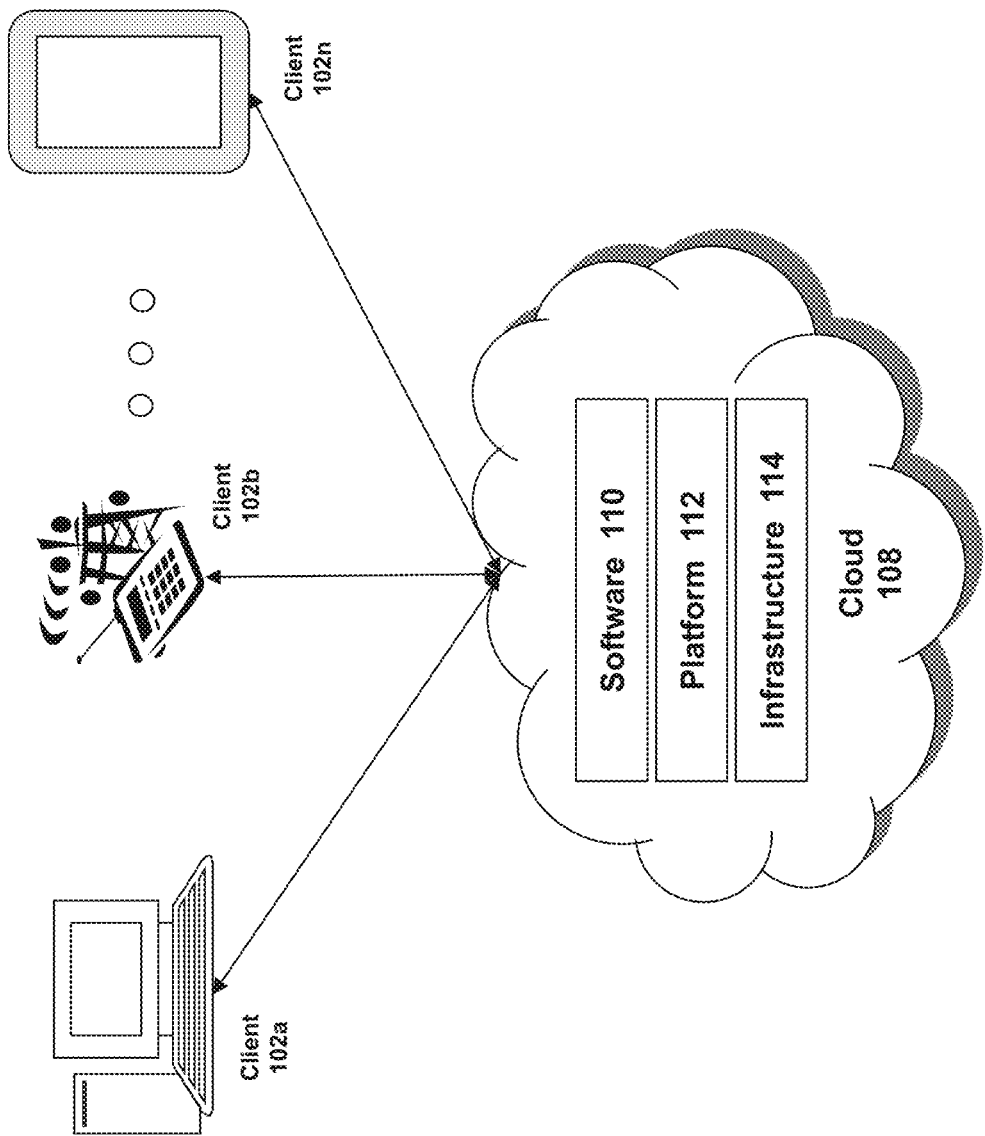
FIG. 1B illustrates an example cloud computing environment including a client device in communication with cloud service providers, in accordance with present implementations.

Referring to FIG. 1B, a cloud computing environment is depicted. A cloud computing environment can provide client 102 with one or more resources provided by a network environment. The cloud computing environment can include one or more clients 102a-102n, in communication with the cloud 108 over one or more networks 104. Clients 102 can include, e.g., thick clients, thin clients, and zero clients. A thick client can provide at least some functionality even when disconnected from the cloud 108 or servers 106. A thin client or a zero client can depend on the connection to the cloud 108 or server 106 to provide functionality. A zero client can depend on the cloud 108 or other networks 104 or servers 106 to retrieve operating system data for the client device. The cloud 108 can include back end platforms, e.g., servers 106, storage, server farms or data centers.

The cloud 108 can be public, private, or hybrid. Public clouds can include public servers 106 that are maintained by third parties to the clients 102 or the owners of the clients. The servers 106 can be located off-site in remote geographical locations as disclosed above or otherwise. Public clouds can be connected to the servers 106 over a public network. Private clouds can include private servers 106 that are physically maintained by clients 102 or owners of clients. Private clouds can be connected to the servers 106 over a private network 104. Hybrid clouds 108 can include both the private and public networks 104 and servers 106.

The cloud 108 can also include a cloud based delivery, e.g. Software as a Service (SaaS) 110, Platform as a Service (PaaS) 112, and Infrastructure as a Service (IaaS) 114. IaaS can refer to a user renting the use of infrastructure resources that are needed during a specified time period. IaaS providers can offer storage, networking, servers or virtualization resources from large pools, allowing the users to quickly scale up by accessing more resources as needed. Examples of IaaS can include infrastructure and services (e.g., EG-32) provided by OVH HOSTING of Montreal, Quebec, Canada, AMAZON WEB SERVICES provided by Amazon.com, Inc., of Seattle, Wash., RACKSPACE CLOUD provided by Rackspace US, Inc., of San Antonio, Tex., Google Compute Engine provided by Google Inc. of Mountain View, Calif., or RIGHTSCALE provided by RightScale, Inc., of Santa Barbara, Calif. PaaS providers can offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Wash., Google App Engine provided by Google Inc., and HEROKU provided by Heroku, Inc. of San Francisco, Calif. SaaS providers can offer the resources that PaaS provides, including storage, networking, servers, virtualization, operating system, middleware, or runtime resources. In some implementations, SaaS providers can offer additional resources including, e.g., data and application resources. Examples of SaaS include GOOGLE APPS provided by Google Inc., SALESFORCE provided by Salesforce.com Inc. of San Francisco, Calif., or OFFICE 365 provided by Microsoft Corporation. Examples of SaaS can also include data storage providers, e.g. DROPBOX provided by Dropbox, Inc. of San Francisco, Calif., Microsoft SKYDRIVE provided by Microsoft Corporation, Google Drive provided by Google Inc., or Apple ICLOUD provided by Apple Inc. of Cupertino, Calif.

Clients 102 can access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards can allow clients access to resources over HTTP, and can use Representational State Transfer (REST) protocol or Simple Object Access Protocol (SOAP). Clients 102 can access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that can be built on REST, HTTP, XML, or other protocols. Clients 102 can access SaaS resources through the use of web-based user interfaces, provided by a web browser (e.g. GOOGLE CHROME, Microsoft INTERNET EXPLORER, or Mozilla Firefox provided by Mozilla Foundation of Mountain View, Calif.). Clients 102 can also access SaaS resources through smartphone or tablet applications, including, e.g., Salesforce Sales Cloud, or Google Drive app. Clients 102 can also access SaaS resources through the client operating system, including, e.g., Windows file system for DROPBOX.

In some implementations, access to IaaS, PaaS, or SaaS resources can be authenticated. For example, a server or authentication server can authenticate a user via security certificates, HTTPS, or API keys. API keys can include various encryption standards such as, e.g., Advanced Encryption Standard (AES). Data resources can be sent over Transport Layer Security (TLS) or Secure Sockets Layer (SSL).

Figure 1C:
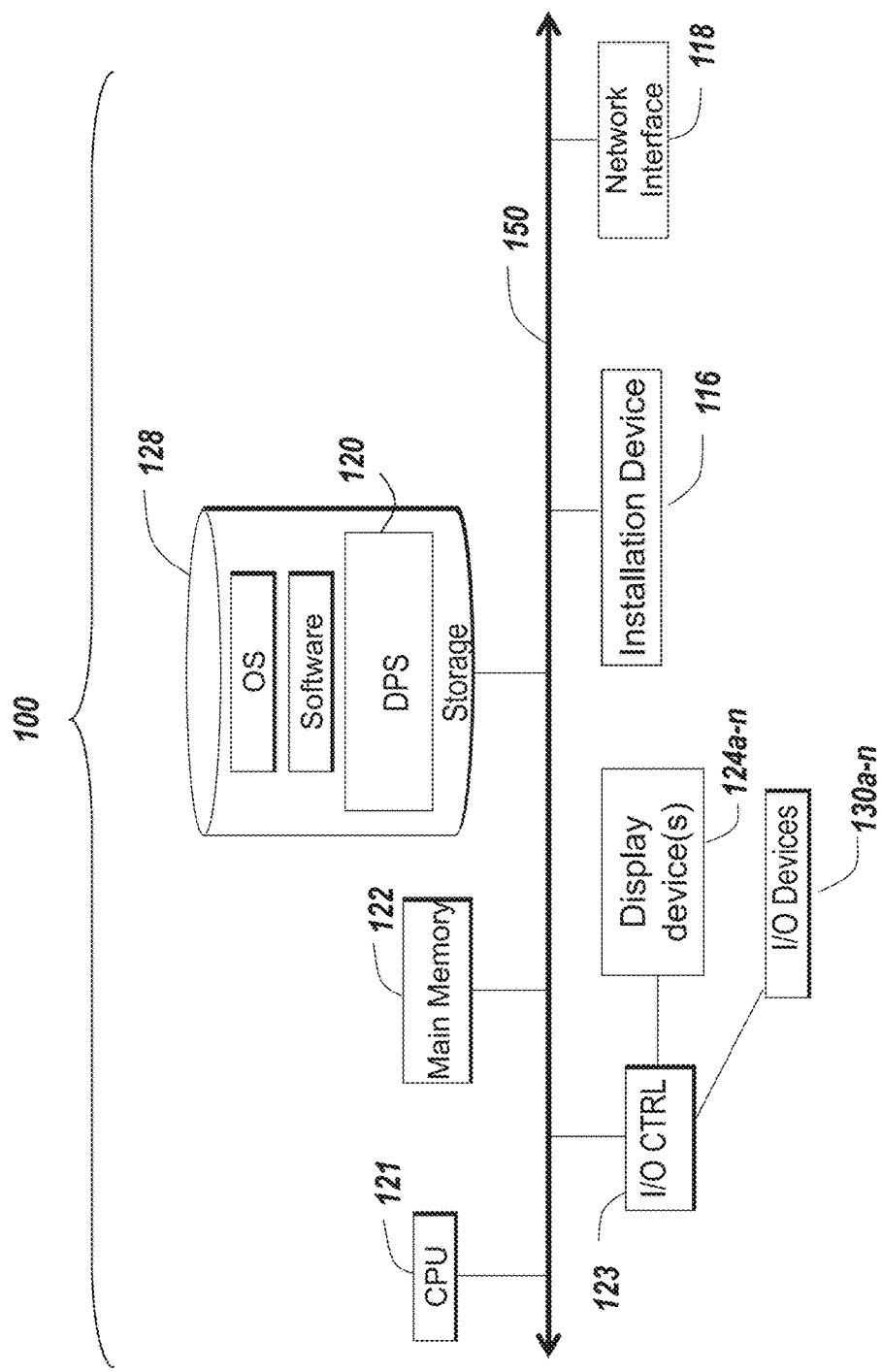
FIGS. 1C and 1D illustrate example computing devices in accordance with present implementations.
Figure 1D:
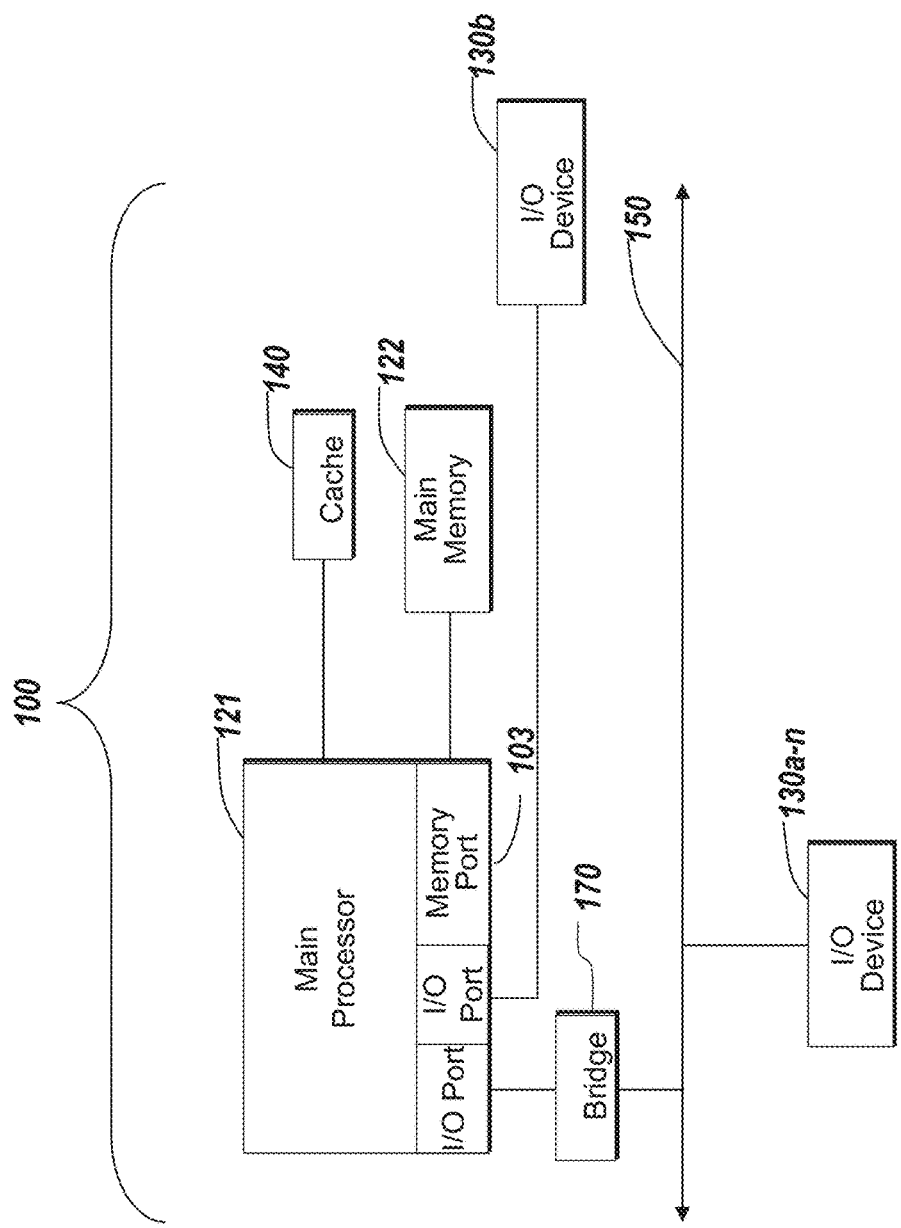

The client 102 and server 106 can be deployed as and/or executed on any type and form of computing device, e.g. a computer, network device or appliance capable of communicating on any type and form of network and performing the operations described herein. FIGS. 1C and 1D depict block diagrams of a computing device 100 useful for practicing an implementation of the client 102 or a server 106. As shown in FIGS. 1C and 1D, each computing device 100 includes a central processing unit 121, and a main memory unit 122. As shown in FIG. 1C, a computing device 100 can include a storage device 128, an installation device 116, a network interface 118, an I/O controller 123, display devices 124a-124n, a keyboard 126 and a pointing device 127, e.g. a mouse. The storage device 128 can include, without limitation, an operating system, software, and a software of an data processing system (DPS) 120. As shown in FIG. 1D, each computing device 100 can also include additional optional elements, e.g. a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many implementations, the central processing unit 121 is provided by a microprocessor unit, e.g.: those manufactured by Intel Corporation of Mountain View, Calif.; those manufactured by Motorola Corporation of Schaumburg, Ill.; the ARM processor and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif. The computing device 100 can be based on any of these processors, or any other processor capable of operating as described herein. The central processing unit 121 can utilize instruction level parallelism, thread level parallelism, different levels of cache, and multi-core processors. A multi-core processor can include two or more processing units on a single computing component. Examples of multi-core processors include the AMD PHENOM IIX2, INTEL CORE i5 and INTEL CORE i7.

Main memory unit 122 can include one or more memory chips capable of storing data and allowing any storage location to be directly accessed by the microprocessor 121. Main memory unit 122 can be volatile and faster than storage 128 memory. Main memory units 122 can be Dynamic random access memory (DRAM) or any variants, including static random access memory (SRAM), Burst SRAM or SynchBurst SRAM (B SRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some implementations, the main memory 122 or the storage 128 can be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 122 can be based on any of the above described memory chips, or any other available memory chips capable of operating as described herein. In the implementation shown in FIG. 1C, the processor 121 communicates with main memory 122 via a system bus 150 (described in more detail below). FIG. 1D depicts an implementation of a computing device 100 in which the processor communicates directly with main memory 122 via a memory port 103. For example, in FIG. 1D the main memory 122 can be DRDRAM.

FIG. 1D depicts an implementation in which the main processor 121 communicates directly with cache memory 140 via a secondary bus, sometimes referred to as a backside bus. In other implementations, the main processor 121 communicates with cache memory 140 using the system bus 150. Cache memory 140 typically has a faster response time than main memory 122 and is typically provided by SRAM, BSRAM, or EDRAM. In the implementation shown in FIG. 1D, the processor 121 communicates with various I/O devices 130 via a local system bus 150. Various buses can be used to connect the central processing unit 121 to any of the I/O devices 130, including a PCI bus, a PCI-X bus, or a PCI-Express bus, or a NuBus. For implementations in which the I/O device is a video display 124, the processor 121 can use an Advanced Graphics Port (AGP) to communicate with the display 124 or the I/O controller 123 for the display 124. FIG. 1D depicts an implementation of a computer 100 in which the main processor 121 communicates directly with I/O device 130b or other processors 121' via HYPERTRANSPORT, RAPIDIO, or INFINIBAND communications technology. FIG. 1D also depicts an implementation in which local busses and direct communication are mixed: the processor 121 communicates with I/O device 130a using a local interconnect bus while communicating with I/O device 130b directly.

A wide variety of I/O devices 130a-130n can be present in the computing device 100. Input devices can include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices can include video displays, graphical displays, speakers, headphones, inkjet printers, laser printers, and 3D printers.

Devices 130a-130n can include a combination of multiple input or output devices, including, e.g., Microsoft KINECT, Nintendo Wiimote for the WII, Nintendo WII U GAMEPAD, or Apple IPHONE. Some devices 130a-130n allow gesture recognition inputs through combining some of the inputs and outputs. Some devices 130a-130n provides for facial recognition which can be utilized as an input for different purposes including authentication and other commands. Some devices 130a-130n provides for voice recognition and inputs, including, e.g., Microsoft KINECT, SIRI for IPHONE by Apple, Google Now or Google Voice Search.

Additional devices 130a-130n have both input and output capabilities, including, e.g., haptic feedback devices, touch-screen displays, or multi-touch displays. Touchscreen, multi-touch displays, touchpads, touch mice, or other touch sensing devices can use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices can allow two or more contact points with the surface, allowing advanced functionality including, e.g., pinch, spread, rotate, scroll, or other gestures. Some touch-screen devices, including, e.g., Microsoft PIXELSENSE or Multi-Touch Collaboration Wall, can have larger surfaces, such as on a table-top or on a wall, and can also interact with other electronic devices. Some I/O devices 130a-130n, display devices 124a-124n or group of devices can be augment reality devices. The I/O devices can be controlled by an I/O controller 123 as shown in FIG. 1C. The I/O controller can control one or more I/O devices, such as, e.g., a keyboard 126 and a pointing device 127, e.g., a mouse or optical pen. Furthermore, an I/O device can also provide storage and/or an installation medium 116 for the computing device 100. In still other implementations, the computing device 100 can provide USB connections (not shown) to receive handheld USB storage devices. In further implementations, an I/O device 130 can be a bridge between the system bus 150 and an external communication bus, e.g. a USB bus, a SCSI bus, a FireWire bus, an Ethernet bus, a Gigabit Ethernet bus, a Fibre Channel bus, or a Thunderbolt bus.

In some implementations, display devices 124a-124n can be connected to I/O controller 123. Display devices can include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays can use, e.g. stereoscopy, polarization filters, active shutters, or autostereoscopy. Display devices 124a-124n can also be a head-mounted display (HMD). In some implementations, display devices 124a-124n or the corresponding I/O controllers 123 can be controlled through or have hardware support for OPENGL or DIRECTX API or other graphics libraries.

In some implementations, the computing device 100 can include or connect to multiple display devices 124a-124n, which each can be of the same or different type and/or form. As such, any of the I/O devices 130a-130n and/or the I/O controller 123 can include any type and/or form of suitable hardware, software, or combination of hardware and software to support, enable or provide for the connection and use of multiple display devices 124a-124n by the computing device 100. For example, the computing device 100 can include any type and/or form of video adapter, video card, driver, and/or library to interface, communicate, connect or otherwise use the display devices 124a-124n. In one implementation, a video adapter can include multiple connectors to interface to multiple display devices 124a-124n. In other implementations, the computing device 100 can include multiple video adapters, with each video adapter connected to one or more of the display devices 124a-124n. In some implementations, any portion of the operating system of the computing device 100 can be configured for using multiple displays 124a-124n. In other implementations, one or more of the display devices 124a-124n can be provided by one or more other computing devices 100a or 100b connected to the computing device 100, via the network 104. In some implementations software can be designed and constructed to use another computer's display device as a second display device 124a for the computing device 100. For example, in one implementation, an Apple iPad can connect to a computing device 100 and use the display of the device 100 as an additional display screen that can be used as an extended desktop. One ordinarily skilled in the art will recognize and appreciate the various ways and implementations that a computing device 100 can be configured to have multiple display devices 124a-124n.

Referring again to FIG. 1C, the computing device 100 can comprise a storage device 128 (e.g. one or more hard disk drives or redundant arrays of independent disks) for storing an operating system or other related software, and for storing application software programs such as any program related to the software 120 for the centralized state processing system. Examples of storage device 128 include, e.g., hard disk drive (HDD); optical drive including CD drive, DVD drive, or BLU-RAY drive; solid-state drive (SSD); USB flash drive; or any other device suitable for storing data. Some storage devices can include multiple volatile and non-volatile memories, including, e.g., solid state hybrid drives that combine hard disks with solid state cache. Some storage device 128 can be non-volatile, mutable, or read-only. Some storage device 128 can be internal and connect to the computing device 100 via a bus 150. Some storage device 128 can be external and connect to the computing device 100 via a I/O device 130 that provides an external bus. Some storage device 128 can connect to the computing device 100 via the network interface 118 over a network 104, including, e.g., the Remote Disk for MACBOOK AIR by Apple. Some client devices 100 may not require a non-volatile storage device 128 and can be thin clients or zero clients 102. Some storage device 128 can also be used as an installation device 116, and can be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 can also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform can facilitate installation of software on a client device 102. An application distribution platform can include a repository of applications on a server 106 or a cloud 108, which the clients 102a-102n can access over a network 104. An application distribution platform can include application developed and provided by various developers. A user of a client device 102 can select, purchase and/or download an application via the application distribution platform.

Furthermore, the computing device 100 can include a network interface 118 to interface to the network 104 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one implementation, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Fla. The network interface 118 can comprise a built-in network adapter, network interface card, PCMCIA network card, EXPRESS-CARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1B and 1C can operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, Calif., among others. Some operating systems, including, e.g., the CHROME OS by Google, can be used on zero clients or thin clients, including, e.g., CHROMEBOOKS.

The computer system 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein. In some implementations, the computing device 100 can have different processors, operating systems, and input devices consistent with the device. The Samsung GALAXY smartphones, e.g., operate under the control of Android operating system developed by Google, Inc. GALAXY smartphones receive input via a touch interface.

In some implementations, the computing device 100 is a gaming system. For example, the computer system 100 can comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Wash.

In some implementations, the computing device 100 is a digital audio player such as the Apple IPOD, IPOD Touch, and IPOD NANO lines of devices, manufactured by Apple Computer of Cupertino, Calif. Some digital audio players can have other functionality, including, e.g., a gaming system or any functionality made available by an application from a digital application distribution platform. For example, the IPOD Touch can access the Apple App Store. In some implementations, the computing device 100 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some implementations, the computing device 100 is a tablet e.g. the IPAD line of devices by Apple; GALAXY TAB family of devices by Samsung; or KINDLE FIRE, by Amazon.com, Inc. of Seattle, Wash. In other implementations, the computing device 100 is an eBook reader, e.g. the KINDLE family of devices by Amazon.com, or NOOK family of devices by Barnes & Noble, Inc. of New York City, N.Y.

In some implementations, the communications device 102 includes a combination of devices, e.g. a smartphone combined with a digital audio player or portable media player. For example, one of these implementations is a smartphone, e.g. the IPHONE family of smartphones manufactured by Apple, Inc.; a Samsung GALAXY family of smartphones manufactured by Samsung, Inc.; or a Motorola DROID family of smartphones. In yet another implementation, the communications device 102 is a laptop or desktop computer equipped with a web browser and a microphone and speaker system, e.g. a telephony headset. In these implementations, the communications devices 102 are web-enabled and can receive and initiate phone calls. In some implementations, a laptop or desktop computer is also equipped with a webcam or other video capture device that enables video chat and video call.

In some implementations, the status of one or more machines 102, 106 in the network 104 are monitored, generally as part of network management. In one of these implementations, the status of a machine can include an identification of load information (e.g., the number of processes on the machine, CPU and memory utilization), of port information (e.g., the number of available communication ports and the port addresses), or of session status (e.g., the duration and type of processes, and whether a process is active or idle). In another of these implementations, this information can be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

B. Generation of a Real-Time Trigger Based Digital Feed

Systems and methods in accordance with present implementations can generate opportunities for consuming healthcare products and services based on detecting various promotions, prices, accounts, or product offerings by a number of healthcare support services. Present implementations can detect state or change in of particular promotions, prices, accounts, or product offerings linked to a healthcare participant and present opportunities for interacting with those promotions, prices, accounts, or product offerings, allowing a user to select one or more of those opportunities and, in response, to modify a healthcare service or modify a pattern of product consumption individualized to that user. Present implementations can thus include an event control engine to govern interactions with external healthcare systems, an opportunity engine to generate, execute, and manage opportunities associated with various external healthcare systems and a participant user of those healthcare systems, and a database system to structure, modify, and manage relationships of and between the participant user, the opportunities, and the external healthcare systems.

To govern interaction with external healthcare systems, an event control engine in accordance with present implementations can include multiple gateways to external systems, and multiple internal systems to control and schedule messages between internal and external systems. Present implementations can include separate gateways configured to interact respectively with third-party healthcare systems and devices associated with individual participants. In some implementations, gateways can include an application programming interface ("API"), security protocol, packetization protocol, for example, to effect communication with external healthcare systems and participant devices. External healthcare systems can also be coupled to internal systems in real-time or near-real-time by these preconfigured and secure interfaces and protocols, allowing a highly responsive and individualized healthcare infrastructure. Real-time or near-real-time communication can include, but is not limited to, reducing or eliminating latency of or delay in communication to below a perceivable level by a user. As one example, latency or delay can be introduced by incompatibilities between third-party computing systems, or databases, and can be reduced or eliminated by interconnection of those systems or databases through automated communication interfaces compatible with both. Participant devices can include smartphones, tablets, personal computers, for example, and can also be in real-time or near-real-time communication with internal systems, and thus, with external systems. Present implementations can include internal systems for generating and managing these real-time or near-real-time communications, which implement highly responsive end-to-end interaction between a participant user of up to multiple healthcare systems and the healthcare systems on which that user relies. Present implementations can also be responsive to real-world conditions in which the system operate, including various limitations on bandwidth and connectivity that participant users and their participant devices may experience, or that healthcare systems may themselves experience. Thus, internal systems in accordance with present implementations can include system scheduling and batch processing of messages between internal systems and the external healthcare systems, participant devices, or both.

To generate and manage opportunities tailored to a particular participant of a particular healthcare service or group thereof, an opportunity engine can discover opportunities by detecting various conditions or states at one or more external healthcare systems relevant to a participant user, audit opportunities to ensure that those opportunities remain relevant and available to an individual participant user, and execute those relevant and available opportunities for the participant user. Both the opportunity discovery and audit systems can be responsive to triggers received from external healthcare systems that are relevant to an individual participant user. For example, a change in prescription drug prices at a particular pharmacy can trigger an opportunity discovery or audit process for a participant if that participant is currently prescribed that prescription drug, for example.

Figure 2:
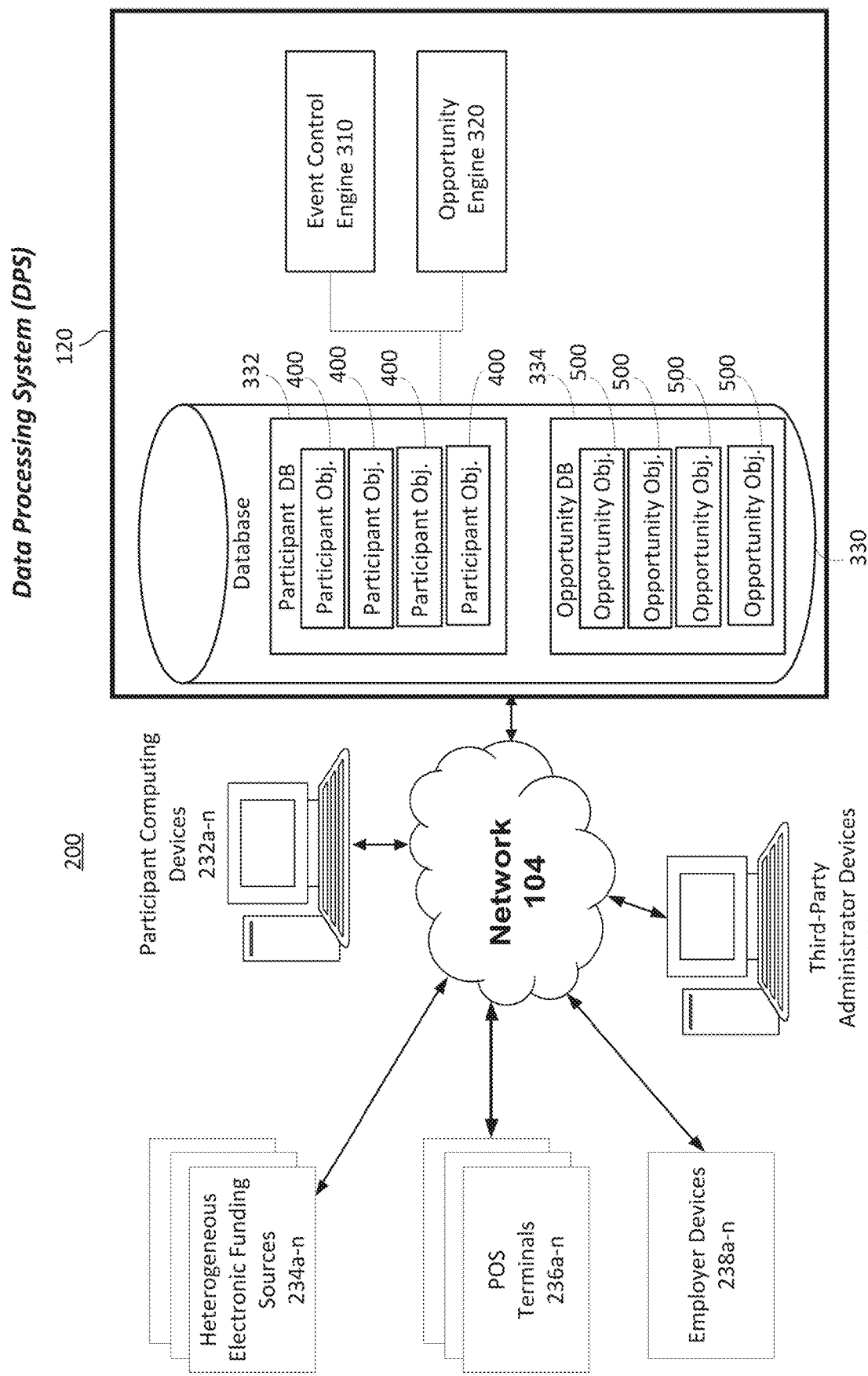
FIG. 2 illustrates an example cloud computing environment including an example data processing system, in accordance with present implementations.

Referring now to FIG. 2, a block diagram depicting an implementation of a system 200 comprising a centralized state processing system is shown. In brief overview, the system 200 includes an data processing system 120 ("DPS") that can receive and/or transmit data via a network 104 with participant computing devices 232a-n, third-party administrator devices 240a-n, employer devices 238a-n, point-of-sale terminals 236a-n, or heterogeneous electronic funding sources 234a-n. The DPS 120 can include a communications interface 204 that is configured with one or more communications ports, application programming interfaces, network protocols (e.g., TCP/IP), authentication protocols, or security protocols (e.g., SSL). The DPS 120 can include, interface with, or otherwise access an event control engine 310 that controls generation, display, and the like, of opportunity objects and participant objects. The DPS 120 can include, interface with, or otherwise access an opportunity engine 320 that analyzes, transmits, executes, and the like, opportunity objects. The DPS 120 can include one or more databases or data structures that store information to facilitate the systems and methods of the present solution, such as database 330. The database 330 can include data structures, files or otherwise categorize information into different databases based at least partially by object. The database 330 can also include one or more policies, profiles, merchant information, or historical transaction activity, and the like.

The system 120, event control engine 310, and opportunity engine 320 can each include one or more processing units or other logic devices such as programmable logic array engines, modules, or circuitry designed and constructed to facilitate managing security on a network infrastructure. The DPS 120 can include the components 100 shown in FIG. 1C or FIG. 1D, or be configured to operate as a service in cloud 108. The DPS 120 can include or interact with one or more servers 106a-n and clients 102a-n. The participant computing devices 232a-n, POS terminals 236a-n, employer devices 238a-n, TPA devices 240a-n, or heterogeneous electronic funding sources 234a-n can each include one or more component or functionality of client computing devices 102a-n or server 106a-n.

In some implementations, the DPS 120 can employ a multitier architecture such as a client-server architecture in which presentation, application processing, and data management functions are logically or physically separated. The presentation tier, or front-end, can include the communications interface 204 that can serve static content or dynamic content to be rendered by the client 102 (e.g., by a web browser executing on client 102). The presentation tier or web server can interact or communicate with the application tier to obtain data to provide to the client 102, computing devices, 232a-n, TPA devices 240a-n, employer devices 238a-n, funding sources 234a-n, or POS terminals 120a-n. The application tier can include the event control engine 310 and the opportunity engine 320. The application tier can interact with the data tier to obtain the transaction data. The data tier can include data persistence mechanisms (database servers, file shares, etc.) and the data access layer that encapsulates the persistence mechanisms and exposes the data. The data tier can include databases 214. The data tier can include an application programming interface (API) to the application tier. The databases 214 can include stored procedures (e.g., SQL statements) that perform tasks with respect the stored data.

The system 200 can include, access, or otherwise communicate with one or more third-party administrator ("TPA") devices 240a-n. A TPA can refer to an organization that processes insurance claims or certain aspects of employee benefit plans for a separate entity. A TPA can refer to organizations within the insurance industry which "administer" other services such as Underwriting or Customer Service. In some cases, a TPA can handle the claims processing for employers 238a-n that self-insures its employees 232a-n. Thus, the employers 238a-n are acting as an insurance company and underwrites the risk. The risk of loss can remains with the employer 238a-n, and not with the TPA 240a-n. An insurance company may also use a TPA 240a-n to manage its claims processing, provider networks, utilization review, or membership functions. The TPA 240a-n can handle many aspects of other employee benefit plans such as the processing of retirement plans and flexible spending accounts. Many employee benefit plans have highly technical aspects and difficult administration that can make using a specialized entity such as a TPA 240a-n more cost effective than doing the same processing in house.

In the health care industry, for example, TPAs 240a-n can administer all or a portion of the claims process. TPAs 240a-n can be contracted by a health insurer or self-insuring companies to administer services, including claims administration, premium collection, enrollment and other administrative activities. For example, an employer 238a-n may choose to help finance the health care costs of its employees 232a-n by contracting with a TPA 240a-n to administer many aspects of a self-funded health care plan.

Administrators, such as companies or health insurance providers, can establish electronic benefits accounts such as flexible spending accounts or healthcare tax benefit accounts (e.g., health savings accounts) for participants such as employees, subscribers, or customers. These electronic benefits accounts can provide a tax advantage for the participants. Administrators that establish or provide electronic tax benefits accounts for various participants of those accounts can utilize backend information technology infrastructure to process, analyze, monitor or manage the electronic tax benefits accounts. The tax benefit management information technology infrastructure can be configured with processing rules that are applied to electronic transactions. Electronic transactions can include allocating funds to the tax benefit account, withdrawing funds from the tax benefit account, making a purchase with funds from the tax benefit account, modifying a profile of the tax benefit account, or submitting a claim. The management information technology infrastructure can apply one or more rules to each type of transaction to determine an event. As the types of transactions and rules increase in number and complexity, the types and events can also increase in number and complexity, thereby consuming an increasing amount of resources of the information technology infrastructure. For example, events such as a card denial increases the number of transaction attempts, communications with the server, account resets, profile corruption, or resources consumed by a point-of-sale device initiating the transaction.

The employer devices 238a-n can refer to a device used by an entity or organization that is associated with the participant computing devices 232a-n of the employees of the employer. For example, Employer A can be a software company that has a thousand employees associated with the participant computing devices 232a-n. The employees can obtain health care or other services, and pay for those services at a POS terminal 236a-n of the service provider.

Data packets can be generated by a device 240a-n at an administrator. The device can refer to an administrator device ("administrator device") such as administrator device 240a-n. The administrator device 240a-n may monitor data from the various electronic benefits accounts associated with the administrator. The accounts associated with the administrator may be accounts that are managed or maintained by the administrator. The administrator may be a point of contact for customers or participants of the associated accounts. In some implementations, the client 102, which may correspond to an individual participant of the administrator's electronic benefits account, may access the account and perform a number of actions with respect to the account, such as, fund the account (e.g., via heterogeneous electronic funding sources 234a-n), withdraw from the account, charge the account, and the like. The administrator of the electronic benefits account, as the caretaker of the account, may adjust parameters associated with the account, such as, monthly fees, minimum running balances, etc. At the same time, the DPS 120 may monitor the data, parameters, and performance of the account and store the information under an administrator profile associated with the administrator of the account. The DPS 120 may receive the data associated with the individual participants and their individual accounts from the client's 102 and the parameter data associated with the accounts from the administrator device 240a-n via the network 104.

An administrator device 240a-n can be the place where an administrator may perform various functions of the administrator, for example, functions associated with electronic benefits accounts of the administrator. The administrator device 240a-n is the point at an administrator that may send requests or transaction information to the DPS 120 for further processing or data collection. The administrator device 240a-n may also be configured to transmit an identifier associated with the administrator corresponding to the administrator device 240a-n for identification by the DPS 120. In some implementations, the receiving of the identifier initiates a fraud detection and control process.

The administrator device 240a-n can include hardware and software. Administrators can utilize scanners, EFTPOS terminals, touch screens and any other wide variety of hardware and software available for use with administrator device 240a-n. For example, an administrator can use software to make adjustments to parameters associated with their electronic benefits accounts.

The administrator device 240a-n can include advanced features to cater to different functionality, such as account participant forecasts and estimates, account simulation, communication with participants of accounts, performing actions associated with individual participant accounts (e.g., freezing an account), collecting data from one or more of the participant accounts, etc., all built into the administrator software. The administrator device 240a-n can be configured to execute user-input commands with respect to the electronic benefits accounts of the administrator.

In some implementations, the communication interface 204 can receive data packets. The data packets can carry one or more electronic transactions. In some cases, the data packets can carry multiple electronic transactions. In some cases, the data packets can be received over a duration of time. The electronic transactions can occur over the duration of time. In some cases, the electronic transaction information carried via the data packets can be received by the DPS 120 in real-time, such as responsive to the occurrence of the electronic transaction. In some cases, the DPS 120 can receive the information about the electronic transactions in a bulk upload or batch upload. Receiving the information about the electronic transactions in a bulk upload or batch upload can reduce computing resource utilization or network bandwidth usage, thereby improving the efficiency of the DPS 120. For example, the provider of the information about the electronic transactions can compress the information and generate data packets carrying the compressed information in a single batch or bulk transmission, thereby reducing network bandwidth utilization.

The electronic transaction information carried via the data packets can include information that facilitates performance of the electronic transaction, or analyzing the electronic transaction to detect fraudulent activity. The electronic transaction can include a source identifier pointing to a data structure storing a resource, a destination identifier corresponding to a data structure to transfer the resource, and an intermediary identifier corresponding to an entity that provides at least a portion of the resource stored in the data structure. The source identifier can refer to an account identifier that contains the resource being transferred from a source to a destination. The source identifier can refer to an account of an employee of an employer. The source identifier can correspond to an account associated with a participant computing device 232. The resource can correspond to an electronic resource or physical resource being represented in an electronic form. The resource can refer to or include a token, currency, points, or other resource that can be transferred from the source to a destination. The destination identifier an correspond to an entity or organization receiving the resource. The destination identifier can correspond to a provider of a service or good that is receiving the resource in return for performing the service or providing the good to the employee. The intermediary identifier can correspond to an entity that stores, holds, manages, provides, or maintains the resource. The intermediary identifier can refer to or correspond to the employer device 238a-n, a heterogeneous electronic funding source 234a-n or TPA 240a-n.

An identifier corresponding to a data structure can refer to or include an identifier pointing to a data structure, such as a memory pointer. The identifier corresponding to a data structure can refer to or include an identifier used by a lookup to retrieve, identify, access or select the data structure. The identifier can label the data structure. The identifier can be mapped to the data structure.

The data packets or electronic transaction can be generated by a device at a merchant to conduct an electronic transaction at the merchant. The device can refer to a point of sale terminal ("POS terminal") such as POS terminal 236a-n. In some implementations, the POS terminals 236a-n are the devices at which retail transactions are initiated. The POS terminals 236a-n are the points at which a customer of the entity or merchant makes a payment to the merchant in exchange for goods or services. At the point of sale the merchant can calculate the amount owed by the customer and provide options for the customer to make payment. The merchant can also issue a receipt for the transaction.

The POS terminal 236a-n can include hardware and software. Merchants can utilize weighing scales, scanners, electronic and manual cash registers, EFTPOS terminals, touch screens and any other wide variety of hardware and software available for use with POS terminal 236a-n. For example, a pharmacy can use software to customize the item or service sold when a customer has a special medication request.

The POS terminal 236a-n can include advanced features to cater to different functionality, such as inventory management, CRM, financials, warehousing, flexible spending account transactions, etc., all built into the POS software. The POS terminal 236a-n can be configured to conduct a transactions using a debit card, multipurse card, Bluetooth, near field communications, smartphone, smartwatch, mobile telecommunications computing device, wearable communications, RFID, etc.

The DPS 120 can include a communications interface 204. The communications interface 204 can execute on one or more processors of a server. The communications interface 204 can include one or more communications ports and be configured with one or more network protocols. Communications ports can include, e.g., network ports, Ethernet ports, WAN ports, I/O ports, or software ports. The communication port can be configured with a network protocol such as Transport Layer Protocols such as TCP/IP or UDP that are configured to receive and process data packets received via a computer network. The port can include or be associated with an IP address of a host and a protocol type of the communication.

The communications interface 204 can receive data packets generated by the POS terminal 236a-n responsive to an electronic transaction resulting in transmission of a request to adjudicate a single claim against an electronic benefits account. In some implementations, the request to adjudicate a single claim against the electronic benefits account is transmitted responsive to a user swiping a payment card at the POS terminal. The payment card can include identifying information that can be used to identify an account identifier of the electronic benefit account (e.g., source identifier) against which to adjudicate the claim. The data packets can include header information and payload information. Multiple data packets can be strung together in a sequence. The header information can refer to TCP/IP headers that include fields such as source port, destination port, sequence number, acknowledge number, window size, etc. The payload information of the data packet can include information related to the electronic transaction, the request to adjudicate a single claim, the merchant, or the customer. The DPS 120 can receive the data packet with header information and payload information and process the packets to obtain information for further processing. The payload can include data identifying the POS terminal 236a-n (e.g., POS terminal 236a) at which the electronic transaction occurred, the merchant providing the POS terminal 236a, a merchant category of the merchant, financial information associated with the user performing the electronic transaction (e.g., via a card swipe or other communication technique used to perform the electronic transaction), an amount of expenditures of the electronic transaction, and other information facilitating adjudication of the single claim. The data packets (e.g., via the payload) can include the request to adjudicate the single claim. The request can specify the electronic benefits account for adjudication. The request can specify information for identifying a policy for performing the adjudication. The payload can include data identifying a merchant category of the merchant, an electronic benefits account, and a monetary amount of the electronic transaction.

The data packets can carry data identifying a merchant or merchant category of the merchant. In some implementations, the data carried by the data packets include a merchant category code or identifier (e.g., dental, medical, etc.). In some implementations, the data identifies a merchant, and the DPS 120 determines a merchant category based on the identification of the merchant by, for example, using a merchant to merchant category mapping or lookup table stored in database. In some implementations, the data packets carrying the request to adjudicate the single claim against the electronic benefits account include a data structure having a first field indicating a merchant identifier, a second field indicating a total amount of expenditures, and a third field indicating the electronics benefit account. In some implementations, the data packets are generated by a merchant device (e.g., a client device 102 of a merchant) to conduct an electronic transaction at the merchant, and the data packets carry data identifying a merchant category of the merchant, the electronic benefits account maintained and configured on the DPS 120, and a total monetary amount of the electronic transaction.

The data packets (e.g., payload of the data packets) can further identify an electronic account maintained and configured on the server. The electronic account can be maintained and configured in a database 214. The electronic account can correspond to a user and have a unique identifier. The unique identifier can include numbers, letters, characters, symbols, etc. The electronic account can be associated with the customer making the transaction at the merchant. The POS terminal 236a can receive or determine the electronic account identifier via a card swipe or other communication technique employed at the POS terminal 236a, which the POS 236a can then convey to the DPS 120.

The communications interface 120 can further receive data packets (e.g., payload information) identifying a monetary amount of the electronic transaction, such as a total amount of expenditures. The monetary amount can be for the purchase of goods or services made at the merchant. The monetary amount of the transaction can refer to the amount of funds in consideration for goods or services obtained from the entity or merchant. The merchant or entity can refer to the entity at which a point-of-sale terminal or device used to make the transaction is located or with which the terminal is associated. The monetary amount can be in any currency (e.g., United States dollars) or units. The monetary amount can be further tied to a category, such as medical services.

In some implementations, the POS terminal 236a can generate multiple data packets for a single transaction. The multiple data packets can each include a header and a payload. The header can indicate that the multiple data packets are to be grouped together for routing, transmission or processing purposes.

Figure 3:
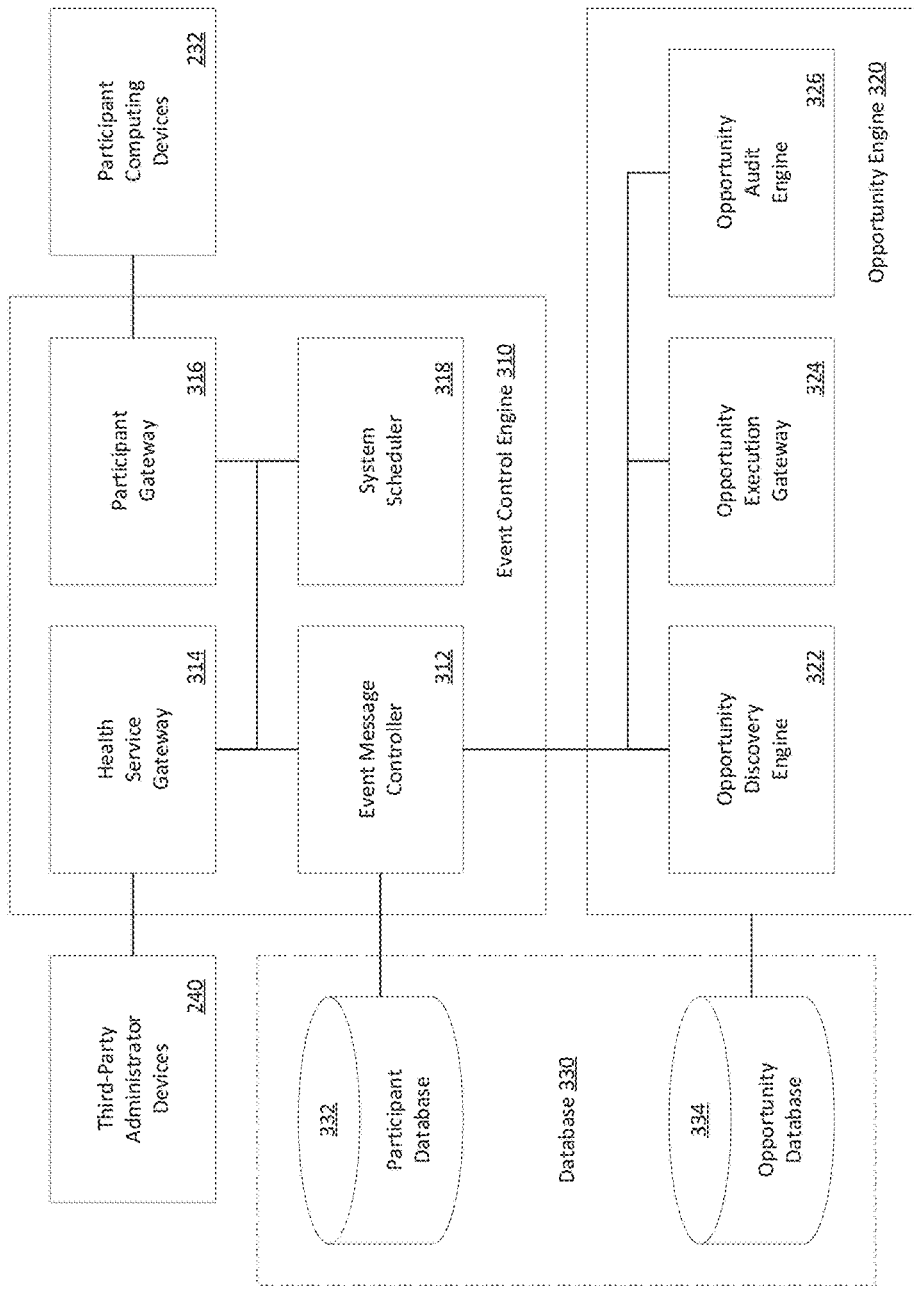
FIG. 3 illustrates an example data processing system, in accordance with present implementations.

FIG. 3 illustrates an example data processing system, in accordance with present implementations. The example data processing system (DPS) 300 can correspond to DPS 120. The DPS 300 can include one or more component or functionality of DPS 120. The DPS 300 can include at least one the event control engine 310. The DPS 300 can include at least one opportunity engine 320. The DPS 300 can include at least one database 330. The event control engine 310 can include at least one event message controller 312. The event control engine 310 can include at least one health service gateway 314. The event control engine 310 can include at least one participant gateway 316. The event control engine 310 can include at least one system scheduler 318. The opportunity engine 320 can include at least one opportunity discovery engine 322. The opportunity engine 320 can include at least one opportunity execution gateway 324. The opportunity engine 320 can include at least one opportunity audit engine 326.

The event control engine 310 can generate, modify, block, transmit, and the like, communication messages between at least the participant computing devices 232, the third party administrator device 240, the opportunity engine 320, and the database 330. The event control engine 310 can include or be associated with one or more operating systems, virtual machines, or interpreters, for example, to generate, modify, block, transmit, or otherwise manage the communication messages. The communication messages can include commands formatted as at least one GET request, PUT request, for example. The event control engine 310 can include one or more logical or electronic devices including but not limited to integrated circuits, logic gates, flip flops, gate arrays, programmable gate arrays, and the like. It is to be understood that any electrical, electronic, or like devices, or components associated with the event control engine 310 can also be associated with, integrated with, integrable with, replaced by, supplemented by, complemented by, for example, a system processor or any component thereof.

The event message controller 312 can restrict, regulate, modify, block, transmit, for example, one or more communication messages according to one or more transmission criteria or security criteria. The event message controller 312 can enforce one or more security policies including one or more security criteria. Here, the event message controller 312 can apply a first security policy to communication messages associated with the participant communication devices 232. Here, the first security policy can include a user level trust zone, associated with a low trust level. Here, the event message controller 312 can apply a second security policy to communication messages associated with the third party administrator devices 240. Here, the second security policy can include a third party level trust zone, associated with a low trust level. Here, the event message controller 312 can apply a third security policy to communication messages associated with the event control engine 310 and the opportunity engine 320. Here, the third security policy can include a cloud trust zone, associated with a medium trust level. It is to be understood that various security policies and various trust zones include, but are not limited to varying numbers and degrees of security encapsulation for example. Here, the security encapsulation can include token validation, password validation, hardware key validation, symmetric encryption key validation, and asymmetric encryption key validation.

The health service gateway 314 can generate one or more communication messages compatible with one or more of the third party administrator devices, based on communication messages received from the event message controller 312. The health service gateway 314 can generate one or more communication messages compatible with the event message controller 312, based on communication messages received from one or more of the third party administrator devices 240. Here, the health service gateway can include at least one application programming interface (API) compatible with the third party administrator devices 240 and the event message controller 312. Here, the health service gateway 314 can include at least one API to interface with third party administrator devices 240 associated with multiple third party administrator services. For example, a third party administrator service can be a participant's health insurance service or a participant's prescription drug records service. Here, the second security policy can securely couple the event control engine 310 to the third party administrator devices by the health service gateway 314, in accordance with one or more health records standards. For example, health records standards may be associated with Health Insurance Portability And Accountability Act (HIPAA) requirements for example.

The participant gateway 316 can generate one or more communication messages compatible with one or more of the participant computing devices 232, based on communication messages received from the event message controller 312. The participant gateway 316 can generate one or more communication messages compatible with one or more of the participant computing devices 232, based on communication messages received from the event message controller 312. Here, the participant gateway 316 can include at least one API compatible with the participant computing devices 232 and the event message controller 312. Here, the participant gateway 316 can encapsulate at least one opportunity object received from the opportunity engine 320 and transmit the encapsulated opportunity object to one or more of the participant computing devices 232. Here, the participant gateway 316 encapsulates an opportunity object in a JSON container, an encrypted package, a compressed package, for example. Here, the participant gateway 316 transmits the opportunity object or the encapsulated opportunity object in accordance with the first security policy.

The system scheduler 318 can generate, modify, block, transmit, and the like, communication messages associated with opportunity objects in accordance with at least one transmission schedule or at least one batch processing criterion. Here, the transmission schedule is a synchronous transmission schedule including at least one transmission interval between transmission times. Here, the event control engine 310 transmits, generates, for example, one or more communication messages associated with opportunity objects at a transmission time. Here, a batch processing criterion can include a connectivity condition between at least one of the participant computing devices 232 and one or more of the event control engine 310 and the data processing system 120. Here, the system scheduler 318 enters an asynchronous mode in response to determining that connectivity with one or more particular participant computing devices 240 is below a connectivity threshold. Here, the batch processing criterion can include the connectivity threshold. As one example, a connectivity threshold can be a minimum lag, bandwidth, uptime, for example associated with a minimum ability to transmit one or more opportunity objects. Here, the system scheduler 318 can include one or more queues to asynchronously store, buffer, for example any communication messages that cannot be transmitted at a particular transmission time due to failure to satisfy a connectivity threshold or satisfying a batch processing criterion. Here, the system scheduler 318 is selectably configurable into a synchronous mode, an asynchronous mode, or both. Here, the system scheduler 318 is selectably configurable by at least one API associated therewith.

The opportunity engine 320 can discover, audit, execute, and the like, one or more opportunity objects. Here, the opportunity engine 320 is operatively coupled to at least one of the participant database 332 and the opportunity database 334 to store, retrieve, modify, generate, link, delete, and the like, one or more objects associated therewith. Here, the opportunity engine 320 is operatively coupled to one or more of the third-party administrator devices 240 by the event control engine 310. Here, the opportunity engine 320 can include one or more logical or electronic devices including but not limited to integrated circuits, logic gates, flip flops, gate arrays, programmable gate arrays, and the like. It is to be understood that any electrical, electronic, or like devices, or components associated with the opportunity engine 320 can also be associated with, integrated with, integrable with, replaced by, supplemented by, complemented by, for example, a system processor or any component thereof.

The opportunity discovery engine 322 can generate one or more opportunity objects. Here, the opportunity discovery engine can generate one or more opportunity objects in response to at least one opportunity trigger. Here, the opportunity discovery engine 322 detects an opportunity trigger based on a change in state of a health support service, support service, health support account, support account, for example associated with a particular participant. Here, the opportunity discovery engine 322 detects the opportunity trigger by a communication message from at least one of the third party administrator devices 240, through the health service gateway 314. Here, an opportunity trigger is based on an opportunity type. As one example, an opportunity trigger can be a change in price for a drug object associated with a participant object. In this example, the opportunity discovery engine 322 determines that an opportunity can be generated or modified for the participant reflecting a price change opportunity, based on the opportunity trigger. As another example, an opportunity object can be a change in preference by a participant to update a preferred pharmacy. In this example, the opportunity discovery engine 322 determines that an opportunity can be generated or modified for the participant reflecting one or more prices associated with drugs available from the newly selected preferred pharmacy, based on the opportunity trigger. In this example, the opportunity discovery engine 322 can generate or modify multiple opportunity objects, if the participant object for the participant is linked to multiple drug objects relevant to the newly selected pharmacy.

The opportunity execution gateway 324 can execute an opportunity object. Here, the opportunity execution gateway 324 receives an opportunity selection, activation, request, for example from one of the participant computing devices 240 by the participant gateway 316 of the event controller engine 310. Here, the opportunity execution gateway generates a communication message and transmits the communication message to one of the third party administrator devices 240 by the health service gateway 314. Here, the health service gateway 314 instructs one or more of the third party devices 240 to execute an operation to modify at least one of a health service, a health service account, or a financial account. As one example, the opportunity execution gateway can instruct a third party pharmaceutical platform to apply a reduced payment to a prescription charge to a financial account associated with the participant and the opportunity. Thus, the opportunity execution gateway can directly effect a transaction outcome with a secure external health support system by the technological solution of the example data processing system in accordance with present implementations. Here, at least one of the opportunity discovery engine 322 and the opportunity audit engine 326 modifies, blocks, deletes, terminates, for example, an opportunity object executed by the opportunity execution gateway 324. Here, at least one of the opportunity discovery engine 322 and the opportunity audit engine 326 conducts a discovery process or an audit process in response to the execution of the opportunity object by the opportunity execution engine 324. Here, the participant computing device 240 associated with the executed opportunity object queries, monitors, polls, for example, the participant gateway 316 to determine whether any opportunity objects or a collection of opportunity objects are changed, or whether updated opportunity objects or a collection of opportunity objects are available for transmission to the participant computing device 240 associated with the executed opportunity object.

The opportunity audit engine 326 can generate one or more opportunity objects. Here, the opportunity trigger associated with the opportunity audit engine 326 corresponds to the opportunity trigger associated with the opportunity discovery engine. Here, the opportunity trigger causes at least one of the opportunity audit engine 326 and the opportunity discovery engine 322 to conduct its respective discovery or audit processes. Here, the opportunity audit engine 326 can convert an opportunity to "complete" in response to receiving an indication of a selection of a particular opportunity object from the participant gateway 316. Here, the opportunity audit engine 326 can convert an opportunity to "expired" in response to determining that the opportunity object fails to satisfy a timestamp threshold associated with the opportunity object. As one example, the opportunity audit engine 326 can convert an opportunity to "expired" in response to determining that a current timestamp occurs at or after a timestamp threshold. Here, the opportunity audit engine 326 modifies a state of an opportunity object or a component, portion, field, value, for example associated with a state of the opportunity object, to convert the opportunity object. Here, the opportunity audit engine 326 changes a state of a collection of opportunities to indicate that an opportunity engine is updated.

Figure 4:
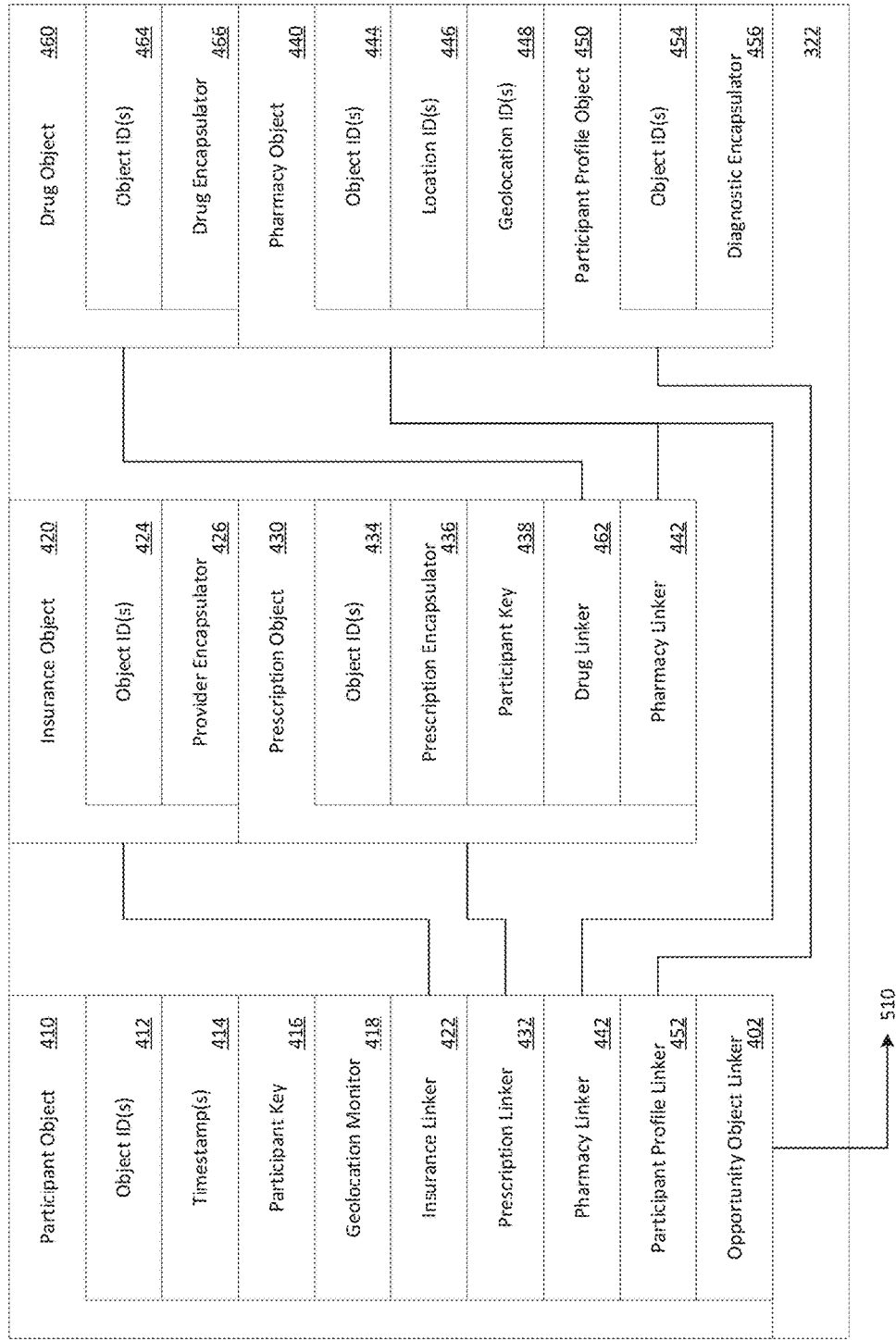
FIG. 4 illustrates an example participant database system further to the example data processing system of FIG. 3, in accordance with present implementations.

FIG. 4 illustrates an example participant database system further to the example data processing system of FIG. 3, in accordance with present implementations. Here, the example participant database system 400 corresponds to the participant database 332. Here, the example participant database system 400 can include at least one of a participant object 410, an insurance object 420, a prescription object 430, a pharmacy object 440, a participant profile object 450, and a drug object 460. It is to be understood that the example participant database system can support an arbitrary number of objects dependent only upon extrinsic characteristics of the example participant database system. As one example, extrinsic characteristics of the example participant database system can include a storage capacity thereof.

The participant object 410 can encapsulate at least one executable, module, link, and the like associated with a participant of a health support system and the like. Here, the participant object can include at least one object identifier 412, timestamp 414, participant key 416, geolocation monitor 418, insurance linker 422, prescription linker 432, pharmacy linker 442, participant profile linker 452, and opportunity object linker 402.

The object identifier 412 contains one or more characteristics associated with a user of the data processing system 120. Here, the object identifier can include one or more of a database key identifying the participant object, a participant identifier associated with a health service, a participant identifier associated with a participant computing device, and the like. As one example, the participant identifier associated with the health service can include at least one an indication of an association between a participant and a particular health service provider, and an association between the participant and a particular health account provider. As another example, the participant identifier associated with the health service can include an indication that the participant is associated with a particular type of health service or health account. As another example, health account type can be an HSA account. The timestamp 414 can indicate one or more times of critical events. Here, the timestamp 414 can include one or more UNIX timestamps. Here, the timestamp 414 can include at least one of a creation timestamp, a modification timestamp. Here, the modification timestamp is responsive to any action to the participant object 410 by the opportunity engine 420 or any component thereof.

The participant key 416 contains a key based on multiple identifiers associated with a participant. Here, the participant key 416 is based on at least one of an account code, an employer identifier and an employee identifier associated with the participant and the health service associated with the participant. Here, the participant key 416 is encrypted, hashed, for example. Here, the participant key 416 is available as a validation key for authorization through the first, second or third security policies.

The geolocation monitor 418 contains a geolocation associated with the participant associated with the participant object 410. Here, the geolocation monitor 418 stores one or more latitude and longitude values to designate a geolocation. Here, the geolocation monitor 418 obtains a geolocation from a participant computing device 240 associated with the participant object 410. Here, the geolocation monitor 418 obtains the geolocation by the participant gateway 316. Here, the event control engine 310 can modify the geolocation monitor 418. Here, the geolocation monitor 418 can receive a geolocation on a constantly updating basis. The geolocation monitor 418 can also receive the geolocation on a scheduled basis in response to actions by the system scheduler 318.

The insurance linker 422 contains a dynamic link to the insurance object 420. Here, the insurance linker 422 can generate, store, for example, a link, reference, for example to the insurance object 420 associated with the participant object 410. Here, the insurance linker 422 associates the insurance object 420 with the participant object 410 in accordance with one or more of an import process of participant information from one or more third party administrator devices 240, or a selection, interaction, for example received from a participant computing device 232 associated with the participant object 410.

The prescription linker 432 contains a dynamic link to the prescription object 430. Here, the prescription linker 432 can generate, store, for example, a link, reference, for example to the prescription object 430 associated with the participant object 410. Here, the prescription linker 432 associates the prescription object 430 with the participant object 410 in accordance with one or more of an import process of participant information from one or more third party administrator devices 240, or a selection, interaction, for example received from a participant computing device 232 associated with the participant object 410.

The pharmacy linker 442 contains a dynamic link to the pharmacy object 440. Here, the pharmacy linker 442 can generate, store, for example, a link, reference, for example to the pharmacy object 440 associated with the participant object 410. Here, the pharmacy linker 442 associates the pharmacy object 440 with the participant object 410 in accordance with one or more of an import process of participant information from one or more third party administrator devices 240, or a selection, interaction, for example received from a participant computing device 232 associated with the participant object 410.

The participant profile linker 452 contains a dynamic link to the participant profile object 450. Here, the participant profile linker 452 can generate or store, for example, a link or reference, for example to the participant profile object 450 associated with the participant object 410. Here, the participant profile linker 452 associates the participant profile object 450 with the participant object 410 in accordance with one or more of an import process of participant information from one or more third party administrator devices 240, or a selection or interaction, for example received from a participant computing device 232 associated with the participant object 410.

The opportunity object linker 402 contains a dynamic link to an opportunity object 510. Here, the opportunity object linker 402 can generate or store, for example, a link or reference, for example to the opportunity object 510 associated with the participant object 410. Here, the participant profile linker 452 associates the participant profile object 450 with the participant object 410 in accordance with one or more of an import process of participant information from one or more third party administrator devices 240, or a selection or interaction, for example received from a participant computing device 232 associated with the participant object 410.

The insurance object 420 can encapsulate at least one executable, module, link, and the like associated with a participant of a health support system and the like. Here, the insurance object is associated with, represents, for example, characteristics, variables, or executables, for example associated with a health support account, or a support account, for example. Here, the insurance object 420 can execute to facilitate execution of one or more instructions to a health support account, or support account, for example. Here, the insurance object 420 can include an object identifier 424 and a provider encapsulator 426. The object identifier 424 contains one or more characteristics associated with an insurance entity associated with the participant object 410 of the data processing system 120. Here, the object identifier 424 contains or can include one or more blocks, links, or executables, for example associated with at least one of the participant object 410 or a participant associated with the participant object 410. The provider encapsulator 426 can encapsulate at least one executable, module, link, and the like associated with a health support system and the like. Here, the object identifier 424 can include one or more identifiers associated with a health support account. As one example, the object identifier 424 can include one or more of a health insurance carrier identification block, a health insurance group identification block, and a health insurance UUID identification block.

The prescription object 430 can encapsulate at least one executable, module, link, and the like associated with a pharmaceutical system, pharmaceutical entity, pharmaceutical account, pharmaceutical, health metric, or biological metric, for example, associated with the participant object 410 or a participant associated with the participant object 410. Here, the prescription object 430 can include an object identifier 434, a prescription encapsulator 436, a participant key 416, a drug linker 462, and a pharmacy linker 442. Here, the prescription object can include corresponding instances, references, for example of one or more elements or components associated with corresponding objects of the example participant database system. The object identifier 434 contains one or more characteristics associated with a pharmaceutical entity associated with the participant object 410 of the data processing system 120. Here, the object identifier 434 can include one or more blocks, links, executables, for example associated with at least one of the participant object 410 or a participant associated with the participant object 410.

The prescription encapsulator 436 can encapsulate at least one executable, module, link, and the like associated with at least one quantity, metric, volume, amount, mass, time, dosage, and the like of at least one drug object 460. Here, the prescription encapsulator can encapsulate at least one personally-identifiable health record within a secure wrapper. Here, the prescription object 430 can securely encapsulate at least one record of any type with the participant key 416. Here, the participant key 416 decrypts for example, either alone or in combination with additional security components, the prescription encapsulator 436 or any wrapper for example associated therewith.

The participant key 438 contains a key based on multiple identifiers associated with a participant. Here, the participant key 438 corresponds to the participant key 416. Here, the participant key 438 is a copy, reference, link, for example, to the participant key 416. Here, the prescription object can validate or facilitate validation of information, executables, parameters, for example, contained in or associated with the participant object 410, the insurance object 420, or the prescription object 430.

The drug linker 462 contains a dynamic link to the drug object 460. Here, the drug linker 462 can generate, store, for example, a link, reference, for example to the drug object 460 associated with the prescription object 430. Here, the drug linker 462 associates the prescription object 430 with the drug object 460 in accordance with one or more of an import process of participant information from one or more third party administrator devices 240, or a selection, interaction, for example received from a participant computing device 232 associated with the participant object 410. Here, the drug linker 462 generates a link, reference, for example to at least one drug object 460 within a prescription associated with a participant object 410. As one example, the drug linker 462 can generate and maintain a link to a drug object statically or dynamically based on a drug provider by a health support service, support service, for example.

The pharmacy linker 442 contains a dynamic link to the pharmacy object 440. Here, the pharmacy linker 442 can generate or store, for example, a link or reference, for example to the pharmacy object 440 associated with the prescription object 430. Here, the pharmacy linker 442 associates the prescription object 430 with the pharmacy object 440 in accordance with one or more of an import process of participant information from one or more third party administrator devices 240, or a selection or interaction, for example received from a participant computing device 232 associated with the participant object 410. Here, the pharmacy linker 442 generates a link or reference, for example to at least one pharmacy object 440 within at least one pharmacy selection criterion associated with a participant object 410. As one example, the pharmacy linker 440 can generate and maintain a link to a pharmacy object statically or dynamically based on a restriction or preference selection by a participant, a restriction or preference by a health support service, or support service, for example.

The pharmacy object 440 can encapsulate at least one executable, module, link, and the like associated with a pharmacy system, pharmacy entity, pharmacy account, health metric, or consumer metric, for example, associated with the participant object 410 or a participant associated with the participant object 410. Here, the pharmacy object 440 can include an object identifier 444, a location identifier 446, and a geolocation identifier 448. The object identifier 444 contains one or more characteristics associated with a pharmacy associated with the participant object 410 of the data processing system 120. Here, the object identifier 444 can include one or more blocks, links, executables, or the like associated with at least one of the participant object 410 or a participant associated with the participant object 410. The location identifier 446 contains one or more characteristics associated with a pharmacy location associated with the participant object 410 of the data processing system 120. Here, the location identifier 446 can include one or more addresses, pharmacy location codes, phone numbers, and the like. The geolocation identifier 448 contains one or more characteristics associated with a pharmacy geolocation associated with the participant object 410 of the data processing system 120. Here, the location identifier 446 can include one or more latitude coordinates, longitude coordinates, spherical coordinates, Global Positioning System ("GPS") coordinates, pathfinding routes, and the like.

The participant profile object 450 can encapsulate at least one executable, module, link, and the like associated with a health metric, consumer metric, diagnostic assessment, prognostic assessment, health device interface, or the like, associated with the participant object 410 or a participant associated with the participant object 410. Here, the participant profile object can include an object identifier 454 and a diagnostic encapsulator 456. The object identifier 454 contains one or more characteristics associated with a pharmacy associated with the participant object 410 of the data processing system 120. Here, the object identifier 454 can include one or more blocks, links, executables, or the like associated with at least one of the participant object 410 or a participant associated with the participant object 410.

The diagnostic encapsulator 456 can encapsulate at least one executable, module, link, and the like associated with at least one characteristic of the participant object 410 or a participant associated with the participant object 410. As one example, diagnostic encapsulator 456 can include at least one of medical history, prescription history, current medical conditions, family medical history, evaluation charts, and the like associated with a participant object 410 or a participant associated with the participant object 410. Here, the diagnostic encapsulator 456 can encapsulate at least one personally-identifiable health record within a secure wrapper. Here, the participant profile object 430 can securely encapsulate at least one record of any type with at least one of the participant key 416 and 438. Here, at least one of the participant key 416 and 438 decrypts or the like, either alone or in combination with additional security components, the prescription encapsulator 436 or any wrapper for example associated therewith. Here, the diagnostic encapsulator 456 can secure information associated therewith or contained therein in accordance with one or more diagnostic security protocols. As one example a diagnostic security protocol can include a restriction on access, decryption, for example, based on a HIPAA or like restriction.

The drug object 460 can encapsulate at least one executable, module, link, and the like associated with a drug, pharmaceutical, chemical, biochemical, composition, substance, element, or molecule, for example associated with at least one of a pharmacy object 440 and a prescription object 430. Here, the drug object 460 is generated based on a database system, inventory system, or sales system, for example associated with at least one of a pharmacy system, health support system, health insurance provider, and the like. As one example, the drug object 460 is generated based on available drugs at one or more pharmacies associated with the participant and included in at least one prescription object associated with the participant. As another example, the drug object 460 is generated based on the diagnostic encapsulator to include drugs associated with a particular health condition of a participant associated with the participant object 410. Here, the drug object can include an object identifier 464 and a drug encapsulator 466. The object identifier 464 contains one or more characteristics associated with a drug object associated with at least one of the participant object 410 and the pharmacy object 440. Here, the object identifier 454 can include one or more blocks, links, or executables, for example associated with at least one of the participant object 410 or a participant associated with the participant object 410.

The drug encapsulator 466 can encapsulate at least one executable, module, link, and the like associated with at least one characteristic of the drug object 460. As one example, the drug encapsulator 466 can include at least one of a chemical composition, commercial product identifier, brand identifier, generic product identifier, and the like. Here, the drug encapsulator 466 can encapsulate at least one personally-identifiable health record within a secure wrapper. Here, the drug object 460 can securely encapsulate at least one record of any type with at least one of the participant key 416 and 438. Here, at least one of the participant key 416 and 438 decrypts for example, either alone or in combination with additional security components, the drug encapsulator 466 or any wrapper for example associated therewith. Here, the drug encapsulator 466 can secure information associated therewith or contained therein in accordance with one or more diagnostic security protocols. As one example a diagnostic security protocol can include a restriction on access, decryption, for example, based on a HIPAA or like restriction.

Figure 5:
FIG. 5 illustrates an example opportunity database system further to the example data processing system of FIG. 3, in accordance with present implementations.

FIG. 5 illustrates an example opportunity database system further to the example data processing system of FIG. 3, in accordance with present implementations. Here, the example opportunity database system 500 corresponds to the opportunity database 334. Here, the example opportunity database system 500 can include at least one of an opportunity object 510, an opportunity type object 520, an opportunity action 530, a prescription action object 540, and an account action object 550.

The opportunity object 510 can encapsulate at least one executable, module, link, and the like associated with a participant of a health support system and the like. Here, the opportunity object 510 is associated with or represents, for example, characteristics, variables, or executables, for example associated with a health support account, or a support account, for example. Here, the opportunity object 510 can execute to facilitate execution of one or more instructions to a health support account, or support account, for example. Here, the opportunity object 510 can execute a financial transaction across a plurality of secure and heterogeneous database system or commercial computing systems. As one example, the opportunity object 510 can execute a transaction with a pharmacy system to obtain a pharmaceutical prescription, including secure patient information and secure financial information of a participant associated with a participant object 410. In this example, the opportunity object 510 achieves the technical solution of secure digital communication across multiple secure systems involving both financial security and patient care security protocols. Here, the opportunity object 510 can include an object identifier 512, a type linker 522, and an action linker 532. The object identifier 512 contains one or more characteristics associated with the opportunity object 510. Here, the object identifier 512 contains or can include one or more blocks, links, or executables, for example associated with opportunity object 510.

The type linker 522 contains a dynamic link to the opportunity type object 520. Here, the type linker 522 can generate, or store, for example, a link, or reference, for example to the opportunity type object 520 associated with the opportunity object 510. Here, the type linker 522 associates the opportunity object 510 with the opportunity type object 520 in accordance with one or more of an import process of participant information from one or more third party administrator devices 240, or a selection, or interaction, for example received from a participant computing device 232 associated with the participant object 410.

The action linker 532 contains a dynamic link to the opportunity action object 530. Here, the action linker 532 can generate, or store, for example, a link, or reference, for example to one or more opportunity action objects 530 associated with the opportunity object 510. Here, the action linker 532 associates the opportunity object 510 with the opportunity action object 530 in accordance with an import process of participant information from one or more third party administrator devices 240 Here, the action linker 532 associates the opportunity object 510 with the opportunity action object 530 in accordance with a selection, or interaction, for example received from a participant computing device 232 associated with the participant object 410. Here, the action linker 532 associates the opportunity object 510 with the opportunity action object 530 in accordance with a scheduled updated initiated by a scheduling process or a batching process.

The opportunity type object 520 can encapsulate at least one executable, module, link, and the like associated with a participant of a health support system and the like. Here, the opportunity object 510 is associated with, or represents, for example, characteristics, variables, or executables, for example associated with an opportunity. As one example, the opportunity type object can include at least one value, metric, executable, or link, for example associated with a time-sensitive opportunity. Here, the opportunity type object 520 can include an object identifier 522 and a point module 524. The object identifier 522 contains one or more characteristics associated with the opportunity type object 510. Here, the object identifier 522 can include one or more blocks, links, or executables, for example associated with opportunity type object 522.

The point module 524 can encapsulate at least one executable, module, link, and the like associated with an execution value of an opportunity object associated with the opportunity type object 520. As one example, the point module 524 includes at least one value, metric, executable, or link, for example associated with a quantitative point value for executing the opportunity object 510. Here, the quantitative point value dynamically changes based on one or more opportunity or participant metrics, factors for example. As one example, the quantitative point value decreases toward zero as a current timestamp approaches a timestamp threshold.

The opportunity action object 530 can encapsulate at least one executable, module, link, and the like to execute or facilitate execution of at least one action based on at least one of the prescription action object 540 and the account action object 550. Here, the opportunity action object 530 can include one or more instructions, restrictions, security policies, interfaces, and the like to execute or facilitate execution of at least one of the prescription action object 540 and the account action object 550. Here, the opportunity action object 530 include an action associated with an application programming interface ("API") of the data processing system 120. Here, the opportunity action objects is associated with an API call through one or more gateways of the data processing system 120. Here, the API call can be a call to conduct actions including SwitchtoDirectDeposit, SetUpMedicineCabinet, ChangeElectronicDelivery, Attach- InsuranceCarrier, AddMobilePhone, SignUpForAlerts, SignUpForElectronicTaxForms, and EnableLocationTracking.

The prescription action object 540 can encapsulate at least one executable, module, link, and the like to execute or facilitate execution of at least one action based on the opportunity action object 540. Here, the prescription action object 540 can include one or more instructions, restrictions, security policies, interfaces, and the like to modify the state of at least one medical records system associated with the prescription action object 540. As one example, a medical records system can include a pharmacy system, a health support system, a health insurance system, and the like. Here, the prescription action object 540 include a cost encapsulator 542, the prescription linker 432, and the pharmacy linker 442.

The cost encapsulator 542 can encapsulate at least one executable, module, link, and the like associated with at least one financial value, metric, for example associated with the prescription object 430. As one example, the cost encapsulator 542 can include at least one of a price, pricing table, pricing modifier associated with at least one of the prescription object 430, the pharmacy object 440, and the drug object 460. Here, the cost encapsulator 542 can generate at least one modification to a cost value, or metric, or the like associated with the prescription object 430, the pharmacy object 440, and the drug object 460. As one example, the cost encapsulator 542 can generate a LongtermSavings value indicating a difference between cost for a prescription upon execution of an opportunity as compared to not executing the opportunity. It is to be understood that the cost encapsulator 542 can achieve the technical solution of generating the LongtermSavings value based on multiple factors including multiple drugs that may be subject to cost modification based on multiple prescriptions from multiple health support systems and multiple pharmacy systems. Here, the cost encapsulator 542 can generate the LongtermSavings value with respect to a plurality of participants based on individualized records.

The account action object 550 can encapsulate at least one executable, module, link, and the like to execute or facilitate execution of at least one action based on the opportunity action object 540. Here, the account action object 550 can include one or more instructions, restrictions, security policies, interfaces, and the like to modify the state of at least one financial account system associated with the account action object 550. As one example, a financial account system can include a bank account, an HSA account, a flexible spending account ("FSA") and the like. Here, the account action object 550 can include an account identifier 552 and a cost encapsulator 554. Here, the account action object 550 can include an account identifier 552 and a cost encapsulator 554. The account identifier 552 contains one or more characteristics associated with the financial account associated with the opportunity action object 530. Here, the account identifier 552 can include one or more blocks, links, or executables, for example associated with a financial account system. As one example, the account identifier 552 is or encapsulates a financial account number, a financial account routing number, a financial account authorization code, a financial account authorization token, or a financial account link, for example.

The cost encapsulator 554 can encapsulate at least one executable, module, link, and the like associated with at least one financial value, or metric, for example associated with the account identifier 552. As one example, the cost encapsulator 542 can include at least one of a financial contribution amount, financial payment amount, financial credit amount, or financial debit amount, for example associated with the account identifier 552. Here, the cost encapsulator 554 can generate at least one modification to a cost value, or metric, for example associated with the account identifier 552. As one example, the cost encapsulator 542 can generate a MaxOutContributions value instructing a financial account system to increase a payment to the financial account according to one or more threshold criteria contained in the account identifier 552. It is to be understood that the cost encapsulator 554 can achieve the technical solution of generating the MaxOutContributions value based on secure direct communication with a financial account system.

Figure 6:
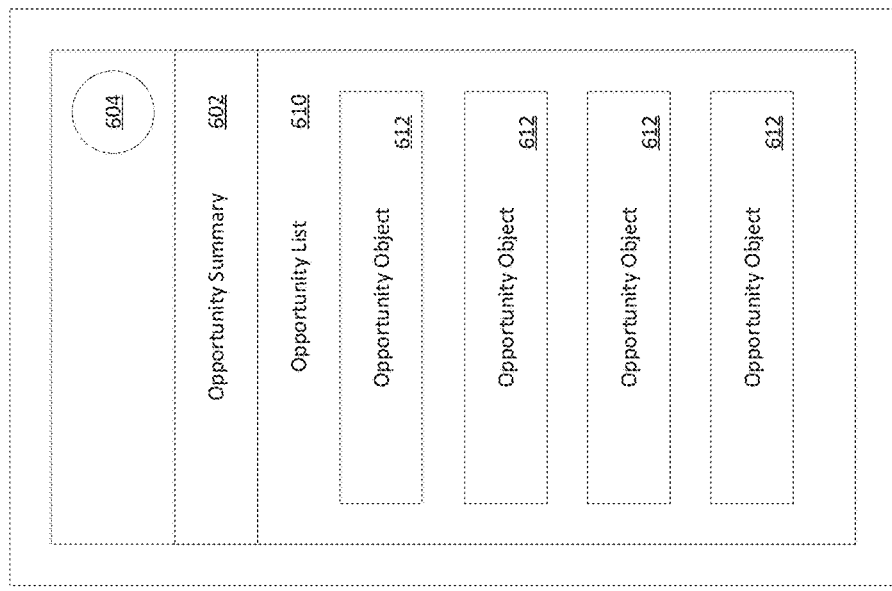
FIG. 6 illustrates an example electronic device associated with an example data processing system, in accordance with present implementations.

FIG. 6 illustrates an example electronic device associated with an example data processing system, in accordance with an implementation. Here, the example electronic device 600 can include a processor, memory device, and display device to generate a graphical user interface, and a communication interface to communication with the data processing system as discussed above with respect to FIGS. 1A-D and 2. Here, the example electronic device can include an opportunity summary region 602, a score summary region 604, an account action object region 606, and an opportunity list region 610. Here, the example electronic device 600 can generate a graphical user interface ("GUI") representing, displaying, and the like, one or more of objects of FIGS. 4 and 5. Here, the example electronic device 600 can include a GUI associated with a mobile operating system. Here, Here, the example electronic device 600 is further operable to receive selection, input, and the like from a touch-based input system disposed thereon, therewith, for example. Here, the touch-based input system is a capacitive or a resistive touch interface. Here, that the mobile interface can include a presentation device including but not limited to an LCD, LED, OLED for example.

The opportunity summary region 602 can present at least one metric associated with one or more opportunity objects available for selection at the example electronic device 600. Here, the opportunity summary region 602 presents a total number of available opportunity objects for selection. Here, the opportunity summary region 602 presents a total number of available opportunity objects that have not yet been executed.

The score summary region 604 can present at least one metric associated with one or more opportunity objects available for selection at the example electronic device 600. Here, the score summary region 604 presents at least one execution value associated with the point module 524. Here, the score summary region 604 presents an aggregation of a plurality of execution values associated with a corresponding plurality of point modules each associated with a particular point value. The opportunity list region 610 can present at least one opportunity object 510 as a selectable GUI element. Here, the opportunity list region can include one or more opportunity objects 612. Here, the opportunity objects 612 each correspond to a distinct opportunity object 510 of a plurality available at the opportunity database 334.

Figure 7:
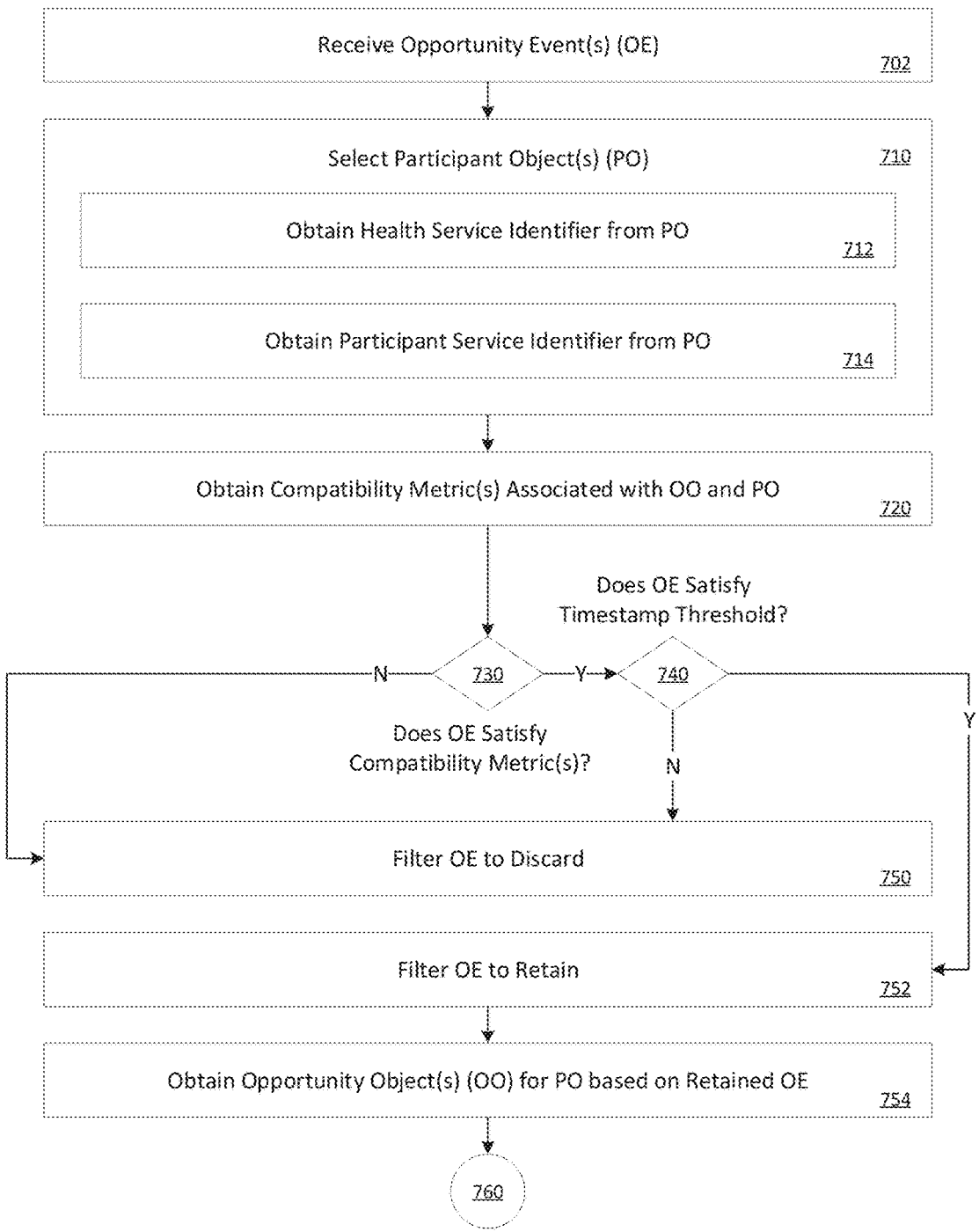
FIG. 7 illustrates an example method of generating a real-time trigger-based digital feed, in accordance with present implementations.

FIG. 7 illustrates an example method of generating a real-time trigger-based digital feed, in accordance with present implementations. The method 700 can be performed by one or more component, system, device or module depicted in FIGS. 1A-6, including, for example, a DPS or device 600. In some implementations, at least one of the example systems 300, 400, and 500 and the example device 600 performs method 700 according to present implementations. The method 700 can be performed by one or more component, system, device or module depicted in FIGS. 1A-6, including for example, a DPS or device 600.

At step 702, the DPS receives at least one opportunity event. The DPS can receive the opportunity event in response to one or more opportunity triggers or in response to an import instruction.

At step 710, the DPS can select at least one participant object. In some implementations, the example system obtains one or more participant objects in accordance with an opportunity trigger. As one example, the DPS can obtain a participant object in response to obtaining an opportunity object associated with a health support service linked to a particular participant object. The example system can generate at least one participant object 410 in response to an import instruction. In some implementations, step 710 includes at least one of steps 712 and 714. At step 712, the DPS can obtain a health service identifier from the participant object. The DPS the health service identifier from the insurance object 420 by the insurance linker 422. At step 714, the DPS obtains a participant service identifier from the participant object. In some implementations, the DPS obtains the participant service identifier from the insurance object 420 by the insurance linker 422. The method 700 then continues to step 720.

At step 720, the DPS obtains at least one compatibility metric associated with at least one of the opportunity object and the participant object. In some implementations, the opportunity discovery engine 322 obtains the compatibility metric. In some implementations, the DPS generates the compatibility metric based on one or more values associated with one or more of the participant profile object 450, the object identifier 454, and the diagnostic encapsulator 456. As one example, the DPS generates a compatibility metric representing a maximum distance to a pharmacy at which an opportunity for a prescription fulfillment can be executed. As another example, the DPS can generate a compatibility metric representing a minimum cost value for redemption of a particular opportunity. As another example, the DPS can generate a compatibility metric blocking opportunities that do not correspond to any account associated with the provider encapsulator, prescription encapsulator, or drug encapsulator associated with a participant object or a participant associated with the participant object. The method 700 then continues to step 730.

At step 730, the DPS determines whether the opportunity event satisfies the compatibility metric. In some implementations, at least one of the opportunity discovery engine 322 and the opportunity audit engine 326 performs step 730. As one example, the opportunity engine blocks all opportunities greater than a maximum threshold distance from a participant address, or geolocation, for example. In accordance with a determination that the opportunity event satisfies the compatibility metric, the method 700 continues to step 740. Alternatively, in accordance with a determination that the opportunity event does not satisfy the compatibility metric, the method 700 continues to step 750. At step 740, the DPS determines whether the opportunity event satisfies at least one timestamp threshold. In some implementations, at least one of the opportunity discovery engine 322 and the opportunity audit engine 326 performs step 750. As one example, the opportunity engine blocks all opportunities with an expiration timestamp after a current time, after a current time minus a travel time, for example. In accordance with a determination that the opportunity event satisfies the timestamp threshold, the method 700 continues to step 752. Alternatively, in accordance with a determination that the opportunity event does not satisfy the timestamp threshold, the method 700 continues to step 750.

At step 750, the DPS filters the opportunity event with a discard action. In some implementations, at least one of the opportunity discovery engine 322 and the opportunity audit engine 326 performs step 750. For example, the DPS can block, deletes, flags, or diverts, for example, an existing opportunity object not satisfying the compatibility metric or the timestamp threshold. In some cases, the DPS can prevent, stop, abort, or terminate generation of an opportunity object not satisfying the compatibility metric or the timestamp threshold. The DPS can generate a candidate opportunity object before satisfaction of any or all required metrics or thresholds, or to forego generation of a candidate opportunity object before satisfaction of any or all required metrics or thresholds. In some implementations, the method 700 ends at step 750. In some implementations, the method 700 then continues to step 702. At step 752, the DPS filter the opportunity event with a retain action. In some implementations, at least one of the opportunity discovery engine 322 and the opportunity audit engine 326 performs step 752. In some implementations, the DPS generates, saves, or stores, for example, an opportunity event to the opportunity database 334 as an opportunity object, or partially generated opportunity object, for example. The method 800 then continues to step 754.

At step 754, the DPS obtains at least one opportunity object associated with the participant object based on a retained opportunity event. In some implementations, the DPS obtains the opportunity object 510 from the opportunity database 334. In some implementations, the opportunity discovery engine 322 performs step 720 in response to a communication message received at the event message controller from at least one of the third party administrator devices 240. As one example, the opportunity discovery engine 322 performs step 720 in response to a communication message from a health system, a pharmacy system, or a financial account system operatively coupled to the DPS indicating a state thereof not associated with an existing opportunity object. In some implementations, the opportunity audit engine 326 performs step 720 in response to a communication message received at the event message controller from at least one of the third party administrator devices 240. As one example, the opportunity audit engine 326 performs step 820 in response to a communication message from a health system, a pharmacy system, or a financial account system operatively coupled to the DPS indicating a change in state to an opportunity object associated therewith. The method 700 then continues to step 730.

Figure 8:
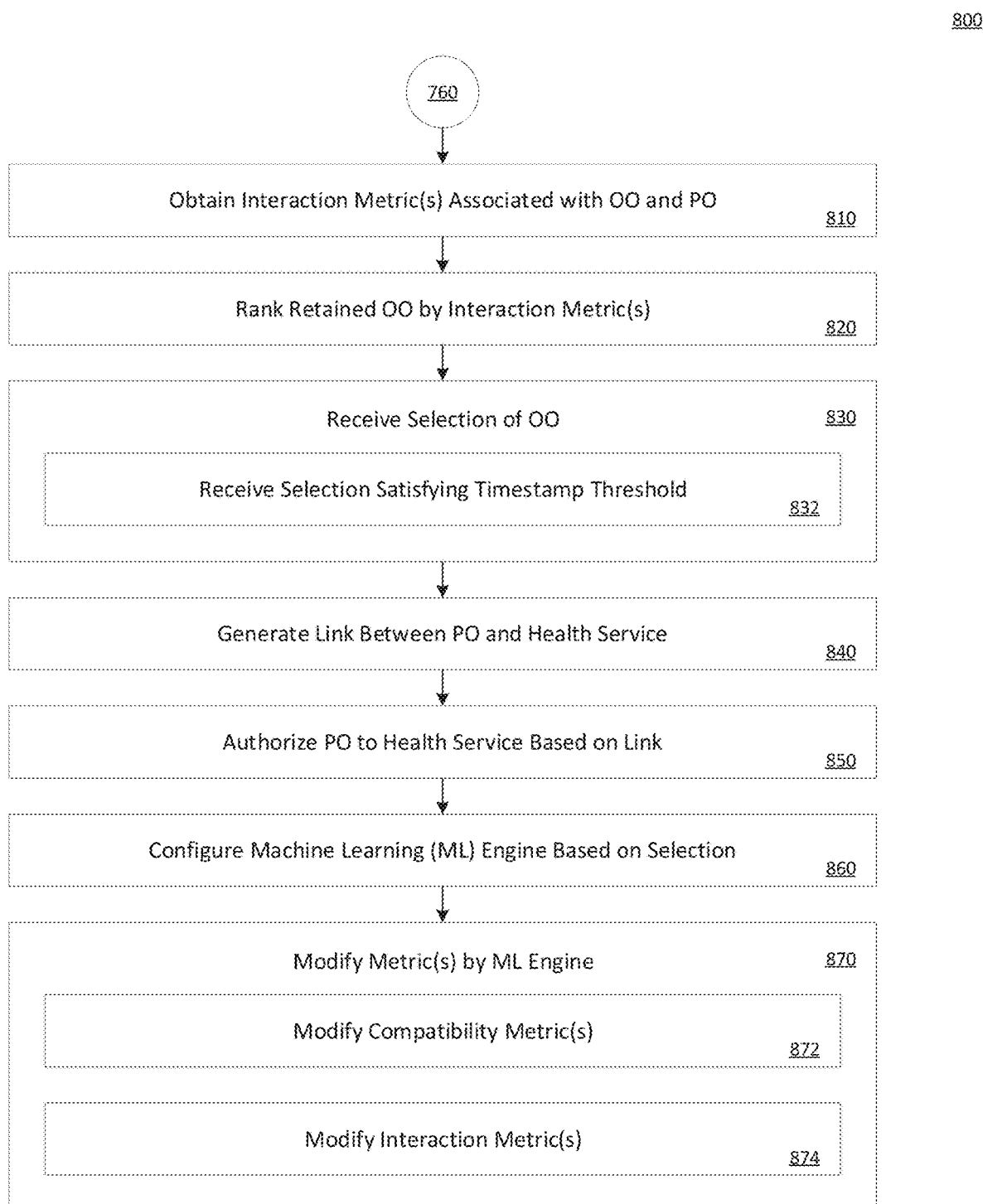
FIG. 8 illustrates an example method of generating a real-time trigger-based digital feed further to the method of FIG. 7, in accordance with present implementations.

FIG. 8 illustrates an example method of generating a real-time trigger-based digital feed further to the method of FIG. 7, in accordance with present implementations. The DPS can perform method 800 according to present implementations. The method 800 can be performed by one or more component, system, device or module depicted in FIGS. 1A-6, including for example, a DPS or device 600.

At step 810, the example system obtains at least one interaction metric associated with at least one of the opportunity object and the participant object. The opportunity discovery engine 322 can obtain the interaction metric. The DPS can generate the interaction metric based on one or more values associated with one or more of the action linker 532, the opportunity action 530, and the opportunity type object 520. The DPS can generate an interaction metric representing a number of times a participant selection of an opportunity matching a particular opportunity type occurs. The interaction metric can represent a frequency of a number of the a participant selection occurs within a predetermined time period. As one example, the interaction metric can represent the number of times a participant selection of a particular prescription opportunity for a particular drug is selected within a month, or with the preceding four weeks. As another example, the example system can generate an interaction metric blocking opportunities that do not correspond to any selection occurrences associated with a participant object or a participant associated with the participant object. The method 800 then continues to step 820.

At step 820, the example system ranks one or more retained opportunity objects by the interaction metric. In some implementations, at least one of the event control engine 310 and the participant gateway 316 performs step 820. The DPS can rank opportunity objects by one or more of timestamp, point value, compatibility metric, and interaction metric. As one example the example system can rank opportunity objects that have the highest interaction metrics or compatibility metrics higher. Ranks of opportunity objects can correspond to higher positions within the opportunity list 610. The method 800 then continues to step 830.

At step 830, the example system receive at least one selection of at least one opportunity object. In some implementations, at least one of the event control engine 310 and the participant gateway 316 performs step 830. The DPS can receive the selection from the example electronic device 600 associated with at least one of the opportunity objects 612. In some implementations, step 830 includes step 832. At step 832, the example system receives at least one selection satisfying a timestamp threshold. The method 800 then continues to step 840.

At step 840, the example system generates at least one link between the participant object and a health service. At least one of the event control engine 310 and the opportunity engine 320 performs step 820. The link can include a communication interface, a communication protocol, or a security protocol allowing execution of one or more communication messages with one or more of the third party administrator devices 240. The method 800 then continues to step 850.

At step 850, the example system authorizes the participant object to the health service based on the generated link. The event control engine can perform step 850. The DPS can authorize the participant object by validating the participant key 416 or 438. The DPS can authorize the participant object to at least one of the event control engine, at least one of the participant computing devices 232, and at least one of the third party administrator devices 240. The method 800 then continues to step 860.

At step 860, the example system configures a machine learning engine based on the selection. In The opportunity engine can perform step 860. The DPS receives as input one or more selection responses from the electronic devices associated with one or more of the participant object 410, the insurance object 420, the prescription objet 430, the pharmacy object 440, the participant profile object 450, the drug object 460, the opportunity object 510, the opportunity type object 520, the prescription action object 540 and the account action object 550, or an component thereof. Thus, the DPS can train and modify a machine learning or like model based on input metrics from one or more of the above. The method 800 then continues to step 870.

At step 870, the example system modifies at least one of the compatibility metric and the interaction metric by the machine learning engine. The opportunity engine can perform step 860. In some implementations, step 870 includes at least one of steps 872 and 874. At step 872, the example system modifies at least one compatibility metric. The DPS can modify the compatibility metric based on a change in state to one or more of the participant profile object 450, the participant object 410, the insurance object 420, the prescription object 430, the pharmacy object 440, and the drug object 460. As one example, the example system modifies the compatibility metric based on a change by a user to a pharmacy preference, or the importing of a new prescription or insurance carrier associated with the participant or the participant object. At step 874, the example system modifies at least one interaction metric. As another example, the example system can modify the interaction metric based on obtaining additional selections of opportunity objects and their associated opportunity action objects from the example electronic device 600. In some implementations, the method 800 ends at step 870.

It should be understood that the systems described above can provide multiple ones of any or each of those components and these components can be provided on either a standalone machine or, in some implementations, on multiple machines in a distributed system. The systems and methods described above can be implemented as a method, apparatus or article of manufacture using programming or engineering techniques to produce software, firmware, hardware, or any combination thereof. In addition, the systems and methods described above can be provided as one or more computer-readable programs embodied on or in one or more articles of manufacture. The term "article of manufacture" as used herein is intended to encompass code or logic accessible from and embedded in one or more computer-readable devices, firmware, programmable logic, memory devices (e.g., EEPROMs, ROMs, PROMs, RAMs, SRAMs, etc.), hardware (e.g., integrated circuit chip, Field Programmable Gate Array (FPGA), Application Specific Integrated Circuit (ASIC), etc.), electronic devices, a computer readable non-volatile storage unit (e.g., CD-ROM, floppy disk, hard disk drive, etc.). The article of manufacture can be accessible from a file server providing access to the computer-readable programs via a network transmission line, wireless transmission media, signals propagating through space, radio waves, infrared signals, etc. The article of manufacture can be a flash memory card or a magnetic tape. The article of manufacture includes hardware logic as well as software or programmable code embedded in a computer readable medium that is executed by a processor. In general, the computer-readable programs can be implemented in any programming language, such as LISP, PERL, C, C++, C#, PROLOG, or in any byte code language such as JAVA. The software programs can be stored on or in one or more articles of manufacture as object code.

The herein described subject matter sometimes illustrates different components contained within, or connected with, different other components. It is to be understood that such depicted architectures are illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent.

The foregoing description of illustrative implementations has been presented for purposes of illustration and of description. It is not intended to be exhaustive or limiting with respect to the precise form disclosed, and modifications and variations are possible in light of the above teachings or may be acquired from practice of the disclosed implementations. It is intended that the scope of the invention be defined by the claims appended hereto and their equivalents.

What is claimed is:

1. A system for invoking account opportunities for support accounts, the system comprising:
    a data processing system comprising memory and one or more processors to:
    receive, from one or more administrator devices external to the data processing system by a first communication interface coupled with the one or more administrator devices, a plurality of opportunity events each indicating a modification to a corresponding transaction at a financial account system external to the data processing system and generated in response to a change to a participant service associated with a participant object;
    select, in response to receipt of the plurality of opportunity events, the participant object including a support service identifier associated with a support service at a corresponding one of the administrator devices, and a participant service identifier associated with the participant service;
    filter the plurality of opportunity events based at least on a first opportunity metric indicating a compatibility between the participant object and one or more of the opportunity events to construct a plurality of opportunity objects;
    rank the plurality of opportunity objects based at least on a determination that the opportunity object satisfies a second opportunity metric associated with the participant object and corresponding to a frequency of selection of the opportunity object via a user interface of a computing device linked with the participant object;
    transmit, to the computing device, the ranked plurality of opportunity objects;
    receive, from the user interface of the computing device presenting the ranked plurality of opportunity objects, a selection of one or more of the ranked plurality of opportunity objects;
    generate, responsive to the selection of the one or more of the ranked opportunity objects, a link between the participant object and the support service; and
    instruct, by a second communication interface coupled with the financial account system, the financial account system to change a state of the support service linked to the participant object.

2. The system of claim 1, wherein the data processing system further comprises a machine learning engine communicatively coupled to the memory and the one or more processors, and is operable to:
configure, by the processor, the machine learning engine based at least partially on the received selection of the one or more ranked opportunity objects by modifying at least one of the first opportunity metric and the second opportunity metric.

3. The system of claim 1, wherein the data processing system is further operable to:
filter, by the processor, the opportunity objects based at least partially on a determination that one or more of the opportunity objects satisfy a timestamp threshold associated with the participant object.

4. The system of claim 3, wherein the received selection is received at a selection time satisfying the timestamp threshold.

5. The system of claim 1, wherein the data processing system is further operable to modify, via machine learning, at least one of the first opportunity metric and the second opportunity metric.

6. The system of claim 1, wherein the first opportunity metric comprises a participant compatibility metric associated with the participant service and the support service.

7. The system of claim 1, wherein the second opportunity metric comprises a participant interaction metric associated with the participant object and at least one of the opportunity objects.

8. The system of claim 1, wherein the opportunity event comprises a state change of the participant object.

9. The system of claim 1, wherein the opportunity event comprises a state change of the participant service.

10. The system of claim 1, wherein the support service identifier identifies a support record of an individual associated with the support service and the participant service.

11. The system of claim 1, wherein the data processing system is further operable to obtain, by the processor, the support service at a remote support account system.

12. The system of claim 1, wherein the data processing system is further operable to obtain, by the processor, the participant service at a remote financial account system.

13. The system of claim 1, wherein the data processing system is further operable to obtain the participant object and the participant service identifier by a first remote communication interface.

14. The system of claim 1, wherein the data processing system is further operable to obtain the opportunity objects by a second remote communication interface.

15. A method for invoking account opportunities for particular support care accounts, the method comprising:
receiving, from one or more administrator devices external to the data processing system by a first communication interface coupled with the one or more administrator devices, a plurality of opportunity events each indicating a modification to a corresponding transaction at a financial account system external to the data processing system and generated in response to a change to a participant service associated with a participant object;
selecting, in response to receipt of the plurality of opportunity events, the participant object including a support service identifier associated with a support service at a corresponding one of the administrator devices, and a participant service identifier associated with the participant service;
filtering the plurality of opportunity events based at least on a first opportunity metric indicating a compatibility between the participant object and one or more of the opportunity events to construct a plurality of opportunity objects;
ranking the plurality of opportunity objects based at least on a determination that the opportunity object satisfies a second opportunity metric associated with the participant object and corresponding to a frequency of selection of the opportunity object via a user interface of a computing device linked with the participant object;
transmitting, to the computing device, the ranked plurality of opportunity objects;
receiving, from the user interface of the computing device presenting the ranked plurality of opportunity objects, a selection of one or more of the ranked plurality of opportunity objects; and
generating, in response to the selection of the one or more of the ranked opportunity objects, a link between the participant object and the support service; and
authorizing, instructing, by a second communication interface coupled with the financial account system, the financial account system to change a state of the support service linked to the participant object.

16. The method of claim 15, further comprising:
configuring a machine learning engine based at least partially on the received selection of the one or more ranked opportunity objects; and
modifying at least one of the first opportunity metric and the second opportunity metric in response to the configuring the machine learning engine.

17. The method of claim 15, wherein the filtering further comprises filtering the opportunity objects based at least partially on a determination that one or more of the opportunity objects satisfy a timestamp threshold associated with the participant object.

18. The method of claim 17, wherein the received selection is received at a selection time satisfying the timestamp threshold.

19. A computer readable medium including one or more instructions stored thereon and executable by a processor to:
receive, from one or more administrator devices external to the data processing system by a first communication interface coupled with the administrator devices, a plurality of opportunity events each indicating a modification to a corresponding transaction at a financial account system external to the data processing system and generated in response to a change to a participant service associated with a participant object;
select, at the processor, in response to receipt of the plurality of opportunity events, the participant object including a support service identifier associated with a support service at a corresponding one of the administrator devices, and a participant service identifier associated with the participant service; and
filter, by the processor, the plurality of opportunity events based at least on a first opportunity metric indicating a compatibility between the participant object and one or more of the opportunity events; and
rank, by the processor, the plurality of opportunity objects based at least on a determination that the opportunity object satisfies a second opportunity metric associated with the participant object and corresponding to a frequency of selection of the opportunity object via a user interface of a computing device linked with the participant object;

transmit, to the computing device, the ranked plurality of opportunity objects;

receive, by the processor and from the user interface the computing device presenting the ranked plurality of opportunity objects, a selection of one or more of the ranked plurality of opportunity objects;

generate, responsive to the selection of the one or more of the ranked opportunity objects, a link between the participant object and the support service; and instruct, by a second communication interface coupled with the financial account system, the financial account system to change a state of the support service linked to the participant object.

20. The computer readable medium of claim 19, wherein the computer readable medium further includes one or more instructions executable by a processor to:

configure a machine learning engine based at least partially on the received selection of the one or more ranked opportunity objects by modifying at least one of the first opportunity metric and the second opportunity metric.

\* \* \* \* \*